(12) United States Patent
Fraser

(10) Patent No.: US 7,217,694 B2
(45) Date of Patent: May 15, 2007

(54) INHIBITORS OF IAPP FIBRIL FORMATION AND USES THEREOF

(75) Inventor: Paul Fraser, Toronto (CA)

(73) Assignee: The Governing Counsel of the University of Toronto, Toronto, Ontario (CA)

( * ) Notice: Subject to any disclaimer, the term of this patent is extended or adjusted under 35 U.S.C. 154(b) by 0 days.

(21) Appl. No.: 09/956,625

(22) Filed: Sep. 19, 2001

(65) Prior Publication Data

US 2002/0119926 A1    Aug. 29, 2002

Related U.S. Application Data

(60) Provisional application No. 60/233,482, filed on Sep. 19, 2000.

(51) Int. Cl.
*A61K 38/08* (2006.01)

(52) U.S. Cl. .......................................... 514/17; 530/329

(58) Field of Classification Search .................... 514/2; 530/329

See application file for complete search history.

(56) References Cited

U.S. PATENT DOCUMENTS 5,124,314 A * 6/1992 Cooper ........................... 514/4
6,087,334 A * 7/2000 Beeley et al. .................. 514/13
6,359,112 B2  3/2002 Kapurniotu et al.

FOREIGN PATENT DOCUMENTS

EP        289287    * 11/1988

OTHER PUBLICATIONS

File CAPLUS on STN. An No. 2003:208785. Scorcchi et al. 'Identification of Minimal Peptide Sequences in the (8-20) Domain of Human Islet Amyloid Polypeptide Involved in Fibrillogenesis.' Journal of Structural Biology. vol. 141. No. 3. pp. 218-227.* (CONT. from U)—2003. Abstract Only.*
Nilsson et al. 'Analysis of Amylin Cleavage products Provides New Insights inot the Amyloidogenic Region of Human Amylin.' J. Mol. Biol. (1999) 294, 1375-1385.*
Jaikaran et al. 'Identification of a Novel Human Islet Amyloid Polypeptide Beta-Sheet Domain and Factors Influencing Fibrillogenesis.' J. Mol. Biol. (2001) 308, 515-525.*
Merlini et al. 'The systemic amyloidoses: clearer understanding of the molecular mechanisms offers hope for more effective therapies', Journal of Internal Medicine (Feb. 2004) 255(2) 159-78.*
Redondo et al. 'Designing transthyretin mutants affecting telrameric structure: implications in amyloidogenicity' Biochemical journal, (May 15, 2000) 348 Pt 1 167-72.*
Rudinger et al., "Peptide Hormones" (Jun. 1976) Ed. J.A. Parsons, Univ. Park Press, Baltimore, pp. 1-7.*

(Continued)

*Primary Examiner*—Anish Gupta
(74) *Attorney, Agent, or Firm*—Clark & Elbing LLP

(57) ABSTRACT

New antifibrillogenic agents and compositions containing same, methods of using the antifibrillogenic agents and compositions for inhibiting amyloid fibril formation, and effective therapeutics for preventing or delaying the progression of, e g., Alzheimer's disease and diabetes.

16 Claims, 25 Drawing Sheets

```
1              10              20              30              40
DAEFRHDSGY EVHHQKLVFF AEDVGSNKGA IIGLMVGGVV IA
|-- Disordered?--|--------β-Sheet Domain-------| Turn |---β-Sheet Domain---|
```

OTHER PUBLICATIONS

Betsholtz et al. (1989). *FEBS Lett 251*: 261-264.
Clark et al. (1993). *Diabetologia 36*: A136 ABSTRACT No. 520.
Clodi et al. (1998). *Am. J. Physiol. 274*: E903-E908.
de Koning et al. (1993). *Diabetologia 36*: 378-384.
Fraser et al. (1994). *J. Mol. Biol. 244*(1): 64-73.
Glenner and Wong (1984). *Biochem. Biophys. Res. Comm. 120*: 885-890.
Glenner and Wong (1984). *Biochem. Biophys. Res Comm. 122*: 1131-1135.
Griffiths et al. (1995). *J. of the Am. Chem. Soc. 12*: 3539-3546.
Higham et al. (2000). *Eur. J. Biochem. 267*: 4998-5004.
Higham et al. (2000). *FEBS Lett 470*: 55-60.
Hubbard et al. (1991). *Biochem. J. 275*: 785-788.
Jarret et al. (1993). *Biochemistry 32*: 4693-4697.
Jarret and Lansbury (1993). *Cell 73*: 1055-1058.
Johnson et al. (1989). *N. Engl. J. Med. 321*: 513-518.
Kahn et al. (1997). *Diabetes 46*: 1725-1732.
Kayed et al. (1999). *J. Mol. Biol. 287*: 781-796.
Lorenzo et al. (1994). *Nature 368*: 756-760.
Moriarty and Raleigh (1999). *Biochemistry 38*: 1811-1818.
Nilsson and Raleigh (1999). *J. Mol. Biol. 294*: 1375-1385.
Opie (1900). *J. Exp. Med. 5*: 397-428.
Saldanha and Mahadevan (1991). *Protein Eng. 4*: 539-544.
Serpell et al. (2000). *J. Mol. Biol. 300*: 1033-1039.
Tjernberg et al. (1997). *J. Biol. Chem. 272*: 12601-12605.
Westermark and Grimelius (1973). *Acta Path. Microbiol. Scand., sect. A. 81*:291-300.
Wood et al. (1996). *J. Biol. Chem. 271*:4086-4092.

\* cited by examiner

```
1           10          20          30          40
DAEFRHDSGY EVHHQKLVFF AEDVGSNKGA IIGLMVGGVV IA
|-- Disordered?--|--------β-Sheet Domain--------| Turn |----β-Sheet Domain----|
```

Fig. 1

```
         10         20        30
KCNTATCATQRLANFLVHSSNNFGAILSSTNVGSNTY
       ATQRLA    SSNNFG
       TQRLAN     SNNFGA
       QRLANF      NNFGAI
        RLANFL     NFGAIL
         LANFLV     FGAILS
         ANFLVH      GAILSS
          NFLVHS      AILSST
           FLVHSS      ILSSTN
```

Fig. 2

IAPP + TQRLAN [FRA 013]
Fig. 18B 1:10 20,000X
Fig. 18A 1:10 5,000X

IAPP + QRLANF [FRA 014]

IAPP + RLANFL [FRA 015]
Fig. 20B 1:20
Fig. 20A 1:10

IAPP + LANFLV [FRA 016]

IAPP + ANFLVH [FRA 019]
1:10
Fig. 22A 20,000X
1:20
Fig. 22B 20,000X IAPP + NFLVHS [FRA 017]
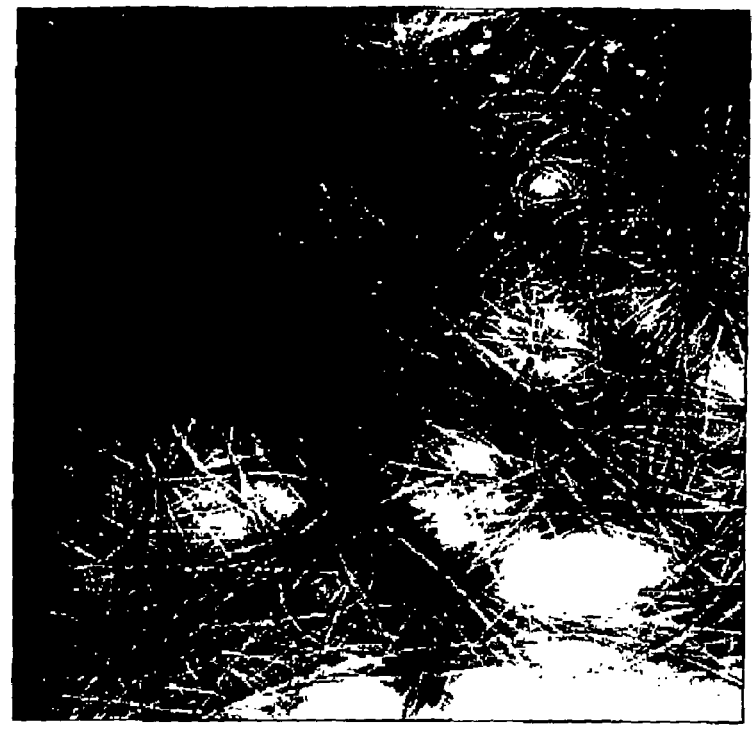
1:10
Fig. 23A  40,000X
1:20
Fig. 23B  40,000X

IAPP + FLVHSS [FRA 018]

INHIBITORS OF IAPP FIBRIL FORMATION AND USES THEREOF

RELATED APPLICATIONS

This application claims the benefit of priority under 35 U.S.C. 119(e) to U.S. Provisional Application No. 60/233,482, filed on Sep. 19, 2000, now abandoned, the entire contents of which are incorporated herein by reference.

BACKGROUND OF THE INVENTION

The invention relates to new antifibrillogenic agents, a composition containing same and a method of using these new antifibrillogenic agents for inhibiting amyloid fibril formation.

Amyloidosis refers to a pathological condition characterized by the presence of amyloid fibers. Amyloid is a generic term referring to a group of diverse but specific protein deposits (intracellular and/or extracellular), which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common x-ray diffraction and infrared spectra.

Amyloid-related diseases can either be restricted to one organ or spread to several organs. The first instance is referred to as "localized amyloidosis" while the second is referred to as "systemic amyloidosis".

Some amyloidotic diseases can be idiopathic, but most of these diseases appear as a complication of a previously existing disorder. For example, primary amyloidosis can appear without any other pathology or can follow plasma cell dyscrasia or multiple myeloma. Secondary amyloidosis is usually seen associated with chronic infection (such as tuberculosis) or chronic inflammation (such as rheumatoid arthritis). A familial form of secondary amyloidosis is also seen in Familial Mediterranean Fever (FMF). This familial type of amyloidosis, as one of the other types of familial amyloidosis, is genetically inherited and is found in specific population groups. In these two types of amyloidosis, deposits are found in several organs and are thus considered systemic amyloid diseases. Another type of systemic amyloidosis is found in long-term hemodialysis patients. In each of these cases, a different amyloidogenic protein is involved in amyloid deposition.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the plaque and blood vessel amyloid is formed by the deposition of fibrillar Aβ amyloid protein. Other diseases such as adult-onset diabetes (Type II diabetes) are characterized by the localized accumulation of amyloid in the pancreas. Amyloid deposits are present in pancreatic islets of up to 96% of patients with Non-Insulin Dependent Diabetes (NIDDM) at post-mortem. These fibrillar accumulations result from the aggregation of the islet amyloid polypeptide (IAPP), also known as amylin.

Once these amyloids have formed, there is no known, widely accepted therapy or treatment which significantly dissolves the deposits in situ.

Each amyloidogenic protein has the ability to organize into β-sheets and to form insoluble fibrils that get deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, will show similarities such as regions with the ability to bind to the glycosaminoglycan (GAG) portion of proteoglycan (referred to as the GAG binding site) as well as other regions which will promote β-sheet formation.

This suggests that amyloid fibrils are formed by a similar protein misfolding pathway and therefore therapeutic interventions to control their folding may be beneficial for all amyloid proteins. The associated proteins are the amyloid-β (Aβ) protein in AD and the islet amyloid polypeptide (IAPP) in Type-II diabetes. In both AD and Type-II diabetes, amyloid plays a key role which suggests that prevention of plaque formation will have significant therapeutic benefits.

In specific cases, amyloidotic fibrils, once deposited, can become toxic to the surrounding cells. As per example, the Aβ fibrils organized as senile plaques have been shown to be associated with dead neuronal cells and microgliosis in patients with Alzheimer's disease. When tested in vitro, Aβ peptide was shown to be capable of triggering an activation process of microglia (brain macrophages), which would explain the presence of microgliosis and brain inflammation found in the brain of patients with Alzheimer's disease.

In another type of amyloidosis seen in patients with Type II diabetes, and in patients with Type I diabetes post-transplantation, the amyloidogenic protein IAPP has been shown to induce β-islet cell toxicity in vitro. Hence, appearance of IAPP fibrils in the pancreas of Type II or Type I diabetic patients could contribute to the loss of the β islet cells (Langerhans) and organ dysfunction.

People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals (dystrophic neurites). A main constituent of these amyloid plaques is the amyloid-β peptide (Aβ), a 40-42 amino-acid protein that is produced through cleavage of the β-amyloid precursor protein (APP). Although symptomatic treatments exist for Alzheimer's disease, this disease cannot be prevented nor cured at this time.

Amyloid-β and Alzheimer's Disease

Deposition of amyloid-β protein (Aβ) fibrils is an invariant feature of AD and is considered to be a major contributing factor to neuronal death and clinical dementia. Aβ is a proteolytic fragment of the β-amyloid precursor protein (βAPP), which accumulates in the neurophils as senile plaques and within cerebral blood vessels. These abnormal filamentous deposits co-localize with dystrophic neurites and reactive gliosis. Similarly, the cerebrovascular amyloid disruption of integral blood brain barriers may be a key factor in eliciting detrimental inflammatory responses leading to neuronal dysfunction. Aβ processing and deposition appear to be pivotal processes in AD pathogenesis which is supported by a number of lines of evidence. The strongest link is provided by the familial AD cases that result from mutations in either the APP or presenilin genes which display abnormal APP processing and herald an early onset and acceleration of the disease process.

Sequencing of Aβ a decade ago provided a catalyst for Alzheimer's research and quickly led to the cloning of the encoding gene. Aβ represents an internal sequence of the membrane-associated amyloid-β precursor protein (APP) that is organized into a large extracellular domain, a single transmembrane helix and a short cytoplasmic tail. Aβ constitutes 28 residues N-terminal to the extracellular-transmembrane interface as well as 12–14 residues of the transmembrane domain.

Previous investigations have demonstrated that synthetic Aβ and its various fragments will spontaneously assemble into amyloid-like fibrils.

In vitro peptide studies have identified important domains within the Aβ sequence, which facilitate aggregation and fibrillogenesis. For example, histidine residues at positions 13 and 14 appear to play a critical role in fibril formation as shown by the pH dependence of the β-conformation (Fraser, P. E. et al., *J Mol Biol* 244(1):64–73, 1994; and Wood et al., *J Biol Chem* 271:4086–4092, 1996). In addition, truncated and mutated peptides indicate that Aβ has two principal β-sheet domains spanning residues 10–25 and 30–42 possibly linked by α-turns. Interactions between both domains are essential for promoting aggregation as exemplified by the observation that small peptides derived from the 10–25 sequence (KLVFFA (SEQ ID NO. 25); residues 16–21) can inhibit fibril formation. Electron microscopy studies of amyloid plaques from AD tissue have revealed that fibrillar Aβ has an additional level of organization, which has been termed "protofilaments" (Serpell et al. *J Mol Biol* 300: 1033–1039, 2000). These small, fibril substructures laterally aggregate to produce the final amyloid fibril.

The C-terminal sequence has been extensively investigated and significant differences between the Aβ1–40 and Aβ1–42 isoforms have been observed (Jarret et al., *Biochemistry* 32:4694–4697, 1993; and Jarret and Lansbury, *Cell* 73:1055–1056, 1993). Peptides containing the final two residues (Leu41-Val42) exhibit increased aggregation and a greater propensity towards fibril formation. The importance of the Aβ42 isoform is further demonstrated by its association with familial forms of AD. Mutations in either the APP or presenilin genes, which are related to early onset AD, all result in significantly elevated levels of the Aβ42, which may represent the nucleating "seed" that initiates Aβ polymerization.

Islet Amyloid Polypeptide and Diabetes

Amyloid deposits are present in pancreatic islets of up to 96% of patients with Non-Insulin Dependent Diabetes (NIDDM) at post-mortem. These fibrillar accumulations result from the aggregation of the islet amyloid polypeptide (IAPP) or amylin, which is a 37 amino acid peptide, derived from a larger precursor peptide, pro-IAPP. IAPP co-localizes and is co-secreted with insulin in response to β-cell secretagogues. This pathological feature is not associated with insulin-dependent diabetes and is a unifying characteristic for the heterogeneous clinical phenotypes diagnosed as NIDDM. The causal factors for islet amyloidosis and its role in the disease process have yet to be determined. However, longitudinal studies in cats and immunocytochemical investigations in monkeys have shown that a progressive increase in islet amyloid is associated with a dramatic decrease in the population of insulin-secreting β-cells and increased severity of the disease. More recently, transgenic approaches have strengthened the relationship of IAPP plaque formation and β-cell dysfunction, which indicates that amyloid deposition is a principal factor in Type-II diabetes.

Islet hyalinosis (amyloid deposition) was first described over a century ago as the presence of fibrous protein aggregates in the pancreas of patients with severe hyperglycemia (Opie, EL., *J Exp. Med.* 5: 397–428, 1990). Today, islet amyloid, composed predominantly of islet amyloid polypeptide (IAPP), or amylin, is a characteristic histopathological marker in over 90% of all cases of Type-II diabetes.

The mature IAPP molecule is a 37 residue peptide synthesized in the pancreas, and is co-localized with insulin in β-cell dense core secretory granules. Since IAPP is co-secreted with insulin, it has been suggested that IAPP plays a role in regulating blood glucose by controlling insulin secretion. The presence of soluble IAPP in the plasma itself is normally not problematic. In patients with Type-II diabetes, however, the accumulation of pancreatic IAPP leads to a buildup of IAPP-amyloid as insoluble fibrous deposits which eventually replace the insulin-producing β cells of the islet resulting in β cell depletion and failure (Westermark, P., Grimelius, L., *Acta Path. Microbiol Scand, sect. A.* 81: 291–300, 1973; de Koning, E J P., et al., *Diabetologia* 36: 378–384, 1993; and Lorenzo, A., et al., *Nature* 368: 756–760, 1994).

The fact that IAPP fibrillar aggregates are present in the pancreases of patients with severe Type-II diabetes and β-cell failure is evident. However, determining whether fibrillar IAPP is toxic to β-cells as well as the conditions that lead to aggregation of this peptide are currently areas of great interest. It has been suggested that differing levels of glycosylation may lead to a pool of peptide that is more apt to be involved in aggregation. Other studies have suggested that in Type-II diabetes, incomplete enzymatic processing of IAPP from its precursor pro-IAPP by the prohormone convertase PC2 may provide a level of aggregatable peptide needed for the "seeding" of amyloid fibrils. Still other studies have examined the properties contained in the amino acid sequence of human IAPP that make it prone to aggregation as compared to rodent IAPP which does not form typical amyloid fibrils (Johnson, K H., et al., *N. Engl. J. Med* 321: 513–518, 1989; and Moriarty, D F., Raleigh, D P. *Biochemistry* 38: 1811–1818, 1999).

IAPP amyloid has many features in common with cerebral amyloid formed in Alzheimer's disease from the amyloid-β ( Aβ) peptide. Both amyloid diseases are progressive and age-related and associated with irreversible deterioration in cellular function. Neither pathological conditions require synthesis of a mutated form of the peptide and both component peptides are derived from a larger precursor and form morphologically similar amyloid fibrils.

IAPP contains three principal domains that contribute to fibril formation. These domains have been identified by looking at different peptide fragments and also through the effects of the proline mutations in the rodent sequence, which does not form amyloid fibrils. The initial N-terminal domain, disulfide bridge (residues 2 and 7) is not critical to amyloid fibril formation.

Diseases caused by the death or malfunctioning of a particular type or types of cells can be treated by transplanting into the patient healthy cells of the relevant type of cell. This approach has been used for Type I diabetic patients. Often these cells are cultured in vitro prior to transplantation to increase their numbers, to allow them to recover after the isolation procedure or to reduce their immunogenicity. However, in many instances the transplants are unsuccessful, due to the death of the transplanted cells. One reason for this poor success rate may be IAPP, which can form fibrils and become toxic to the cells in vitro. In addition, IAPP fibrils are likely to continue to grow after the cells are transplanted and cause death or dysfunction of the cells. This may occur even when the cells are from a healthy donor and when the patient receiving the transplant does not have a disease that is characterized by the presence of fibrils.

SUMMARY OF THE INVENTION

The invention relates to, inter alia, in vitro and in vivo inhibitors of amyloid fibril formation. These inhibitors are, e.g., peptides which are capable of controlling IAPP aggregation and amyloid formation. This property may be used advantageously in other embodiments of the invention as disclosed herein.

In one embodiment, the peptides may be ATQRLAN-FLVHSSSSNNFGAILSSTN (SEQ ID NO. 1); ATQRLAN-FLVHSS (SEQ ID NO. 2); NVGSNTY (SEQ ID NO. 3); SSNNFGAILSSTN (SEQ ID NO. 4); ATQRLA (SEQ ID NO. 5); LANFLV (SEQ ID NO. 6); ANFLVH (SEQ ID NO. 7); NFLVHS (SEQ ID NO. 8); FLVHSS (SEQ ID NO. 9); SSNNFG (SEQ ID NO. 10); SNNFGA (SEQ ID NO. 11); NNFGAI (SEQ ID NO. 12); FGAILS (SEQ ID NO. 13); GAILSS (SEQ ID NO. 14); AILSST (SEQ ID NO. 15); ILSSTN (SEQ ID NO. 16); NVGSNT (SEQ ID NO. 17); or VGSNTY (SEQ ID NO. 18); or isomers, retro or retro-inverso isomers, peptidomimetics or salts thereof. The agents may also be all-[D] isomers, all-[L] isomers, or a mixture of [L] and [D] isomers of the peptide.

These antifibrillogenic agents may advantageously be used in the treatment of, e.g., cultured pancreatic islet cells in vitro prior to transplantation, for the treatment of type I diabetes patients, e.g., post-transplantation, to prevent or inhibit fibril formation in the transplanted cells.

The antifibrillogenic agents and methods of the invention may advantageously be used in preventing or delaying the progression of, notably, diabetes (Type I or Type II), and as inhibitors of fibril formation for controlling folding or deposition of amyloid proteins.

Another embodiment of the invention relates to peptides; or isomers, retro or retro-inverso isomers, peptidomimetics, or salts thereof, for inhibiting amyloidosis and/or for cytoprotection. Such peptides may be ATQRLA (SEQ ID NO. 5), LANFLV (SEQ ID NO. 6), ANFLVH (SEQ ID NO. 7), NFLVHS (SEQ ID NO. 8), FLVHSS (SEQ ID NO. 9), SSNNFG (SEQ ID NO. 10), SNNFGA (SEQ ID NO. 11), NNFGAI (SEQ ID NO. 12), FGAILS (SEQ ID NO. 13), GAILSS (SEQ ID NO. 14), AILSST (SEQ ID NO. 15), ILSSTN (SEQ ID NO. 16), NVGSNT (SEQ ID NO. 17), or VGSNTY (SEQ ID NO. 18).

The invention also provides peptides for inhibiting amyloidosis and/or for cytoprotection, where the peptide binds to a sequence selected from ATQRLANFLVHSSSSNNF-GAILSSTN (SEQ ID NO. 1), ATQRLANFLVHSS (SEQ ID NO. 2), NVGSNTY (SEQ ID NO. 3) SSNNFGAILSSTN (SEQ ID NO. 4), ATQRLA (SEQ ID NO. 5), LANFLV (SEQ ID NO. 6), ANFLVH (SEQ ID NO. 7), NFLVHS (SEQ ID NO. 8), FLVHSS (SEQ ID NO. 9), SSNNFG (SEQ ID NO. 10), SNNFGA (SEQ ID NO. 11), NNFGAI (SEQ ID NO. 12), FGAILS (SEQ ID NO. 13), GAILSS (SEQ ID NO. 14), AILSST (SEQ ID NO. 15), ILSSTN (SEQ ID NO. 16), NVGSNT (SEQ ID NO. 17), and VGSNTY (SEQ ID NO. 18). Upon binding to the sequence, fibril formation and amyloidosis are prevented. The peptide may desirably be SSNNFG (SEQ ID NO. 10), SNNFGA (SEQ ID NO. 11), GAILSS (SEQ ID NO. 14), AILSST (SEQ ID NO. 15), LANFLV (SEQ ID NO. 6) or ANFLVH (SEQ ID NO. 7).

The invention also relates to labeled conjugates for in vivo imaging of amyloid deposits featuring a conjugate of formula I:

(I)

where z is 0 or 1; $A_f$ is an antifibrillogenic agent as defined above; $A_{lnk}$ is a linker moiety; and $A_{lab}$ is a labeling moiety that allows for said in vivo imaging. Desirably, $A_{lab}$ is a radiolabeling moiety, and is more preferably $^{99m}$Tc, $^{99}$Tc, $^{64}$Cu, $^{67}$Cu, $^{97}$Ru, $^{119}$Pd, $^{186}$Re, $^{188}$Re, $^{111}$In, $^{113m}$In, $^{153}$Gd, $^{90}$Y, $^{153}$Sm, $^{116}$Ho, $^{198}$Au, $^{199}$Au, $^{90}$Sr, $^{89}$Sr, $^{115}$Rh, $^{201}$Tl, $^{51}$Cr, $^{67}$Ga, $^{57}$Co, $^{60}$Co, $^{123}$I, $^{125}$I, $^{131}$I or $^{18}$F. The labeled conjugate may also be formulated in a composition for in vivo imaging of amyloid deposits. Such composition may comprise a therapeutically effective amount of a labeled conjugate as defined above in association with a pharmaceutically acceptable carrier.

The invention also includes compositions for the treatment of amyloidosis disorders in a patient, including a therapeutically effective amount of an antifibrillogenic agent as defined above with a pharmaceutically acceptable carrier; and methods for the treatment of amyloidosis disorders in a patient, wherein a therapeutically effective amount of the antifibrillogenic agent is administered to a patient in need of such treatment. In an embodiment, the compositions of the invention may be administered in conjunction with insulin, or in conjunction with sulfonylurea and glucose sensitizers, e.g., in a treatment for diabetes.

Processes for the preparation of cells suitable for transplantation into a mammal, which cells are capable of forming amyloid deposits or of evoking endogenous amyloid deposition once transplanted, are also disclosed. The processes include contacting such cells in vitro with the antifibrillogenic agent. The antifibrillogenic agent causes a breakdown of amyloid deposits (the deposits having been formed by the cells prior to coming in contact with the antifibrillogenic agent). In order to optimize the survival of cells, the cells may desirably be cultured in the presence of the antifibrillogenic agent.

The invention further includes methods for treating Type I diabetes patients post-transplantation, wherein an antifibrillogenic agent of the invention is administered to a Type I diabetes patient, so that amyloid deposit formation and amyloidosis is inhibited, prevented and/or reduced.

The use of antifibrillogenic agents, compositions containing same or compounds as described above for the various methods described above, or for manufacturing a medicament or a composition for use in the various methods described above, are also disclosed.

BRIEF DESCRIPTION OF THE DRAWINGS

FIG. 1 illustrates the sequence of the amyloid-β (Aβ) peptide (SEQ ID NO:26) and its proposed structural domains;

FIG. 2 illustrates hexapeptides to be examined and their correspondence to the primary sequence of IAPP (SEQ ID NO:27). The SEQ ID NOs of the hexapeptides in this figure are in the left hand column, SEQ ID NOs: 5, 22, 23, 24, 6, 7, 8, and 9 from top to bottom respectively. On the hexapeptides in the right hand column have the SEQ ID NOs: 10, 11, 12, 19, 13, 14, 15, and 16;

FIGS. 18A and 18B illustrate electron micrographs of IAPP fibrils after incubation with FRA-013 peptide magnified 5000×(FIG. 18A) or 20,000×(FIG. 18B) for a 1:10 dilution of the peptide;

FIGS. 19A and 19B illustrate electron micrographs of IAPP fibrils after incubation with FRA-014 peptide at 1:10 (FIG. 19A; magnification 2000×) or 1:20 (FIG. 19B; magnification 20,000×) dilution;

FIGS. 20A and 20B illustrate electron micrographs of IAPP fibrils after incubation with FRA-015 peptide at 1:10 (FIG. 20A) or 1:20 (FIG. 20B) dilution;

FIGS. 21A and 21B illustrate electron micrographs of IAPP fibrils after incubation with FRA-016 peptide at 1:10 (FIG. 21A) or 1:20 (FIG. 21B) dilution;

FIGS. 22A and 22B illustrate electron micrographs of IAPP fibrils after incubation with FRA-019 peptide at 1:10 (FIG. 22A) or 1:20 (FIG. 22B) dilution;

FIGS. 23A and 23B illustrate electron micrographs of IAPP fibrils after incubation with FRA-017 peptide at 1:10 (FIG. 23A) or 1:20 (FIG. 23B) dilution;

Figures 24A, 24B:
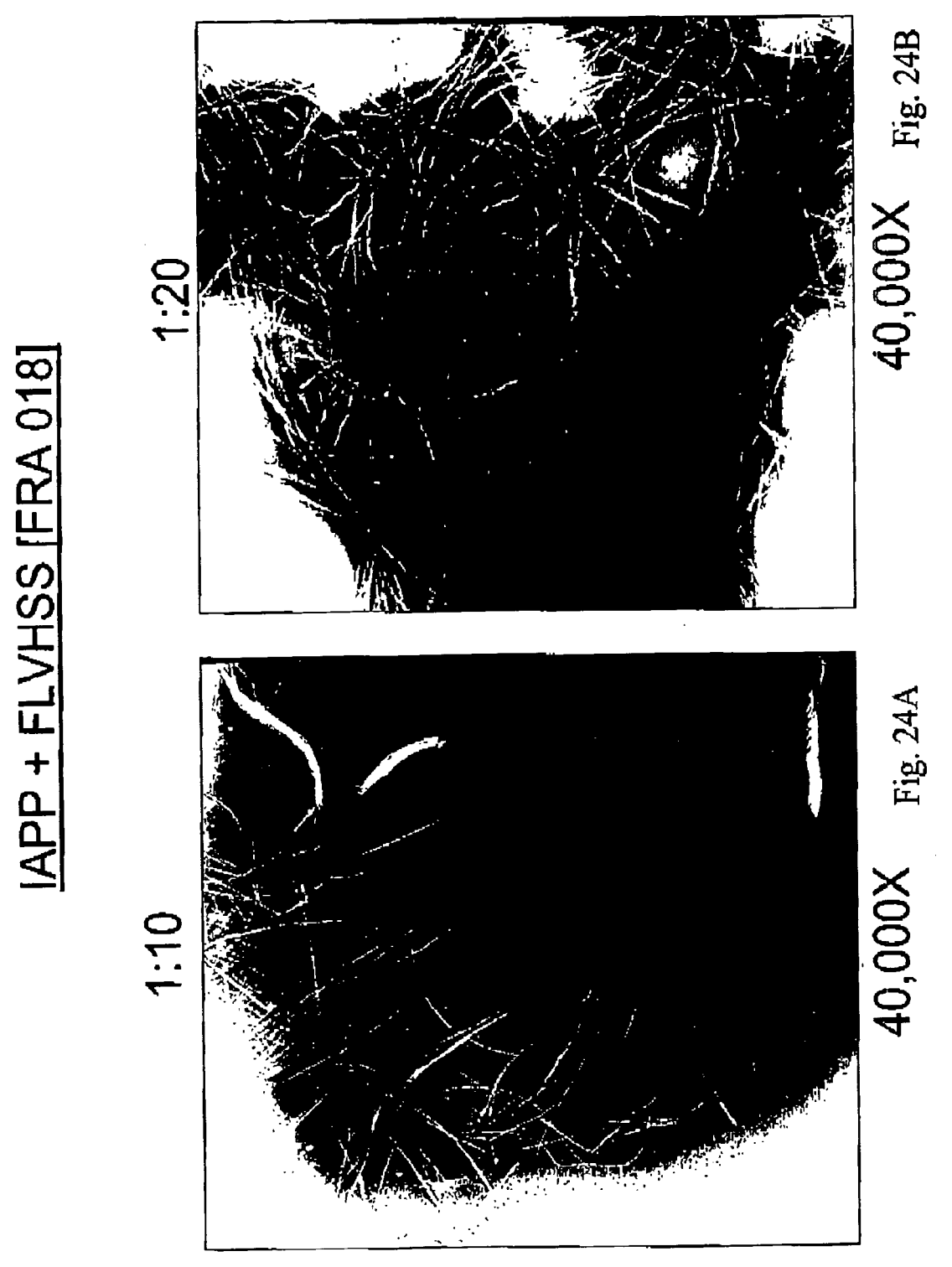

FIGS. 24A and 24B illustrate electron micrographs of IAPP fibrils after incubation with FRA-018 peptide at 1:10 (FIG. 24A) or 1:20 (FIG. 24B) dilution.

DETAILED DESCRIPTION OF THE INVENTION

Figure 3A:
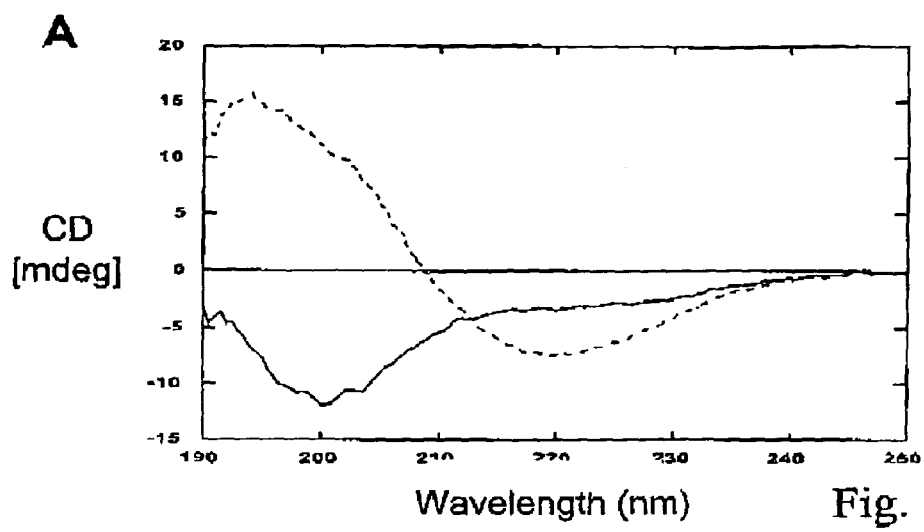
FIGS. 3A to 3C illustrate the conformation of IAPP peptides assessed by protein spectroscopy.

For the purpose of the present disclosure, the following terms are defined below.

The term "peptidomimetic" includes non-peptide compounds which mimic the structural or the functional properties of a peptide.

The term "amyloid related disorders" includes diseases associated with the accumulation of amyloid which can either be restricted to one organ, "localized amyloidosis", or spread to several organs, "systemic amyloidosis". Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, diabetes type II and any related disorders thereof, neurodegenerative diseases such as scrapie, bovine spongiform encephalitis, Creutzfeldt-Jakob disease, Alzheimer's disease, Cerebral Amyloid Angiopathy, and prion protein related disorders. This term also includes AA amyloidoses, AL amyloidoses, hereditary systemic amyloidoses, senile systemic amyloidosis, cerebral amyloidosis, dialysis-related amyloidosis, and hormone-derived amyloidoses.

"Retro isomer" includes molecules, e.g., peptides, having a reversal of the direction of the peptide backbone.

"Peptides" include isomers thereof, retro or retro-inverso isomers thereof, peptidomimetics thereof, all-[D] isomers thereof, all-[L] isomers thereof, a mixture of [L] and [D] isomers thereof; or salts thereof.

"Inverso isomer" includes molecules, e.g., peptides, having a inversion of the amino acid chirality used to make the peptide.

"Retro-inverso isomer" includes molecules, e.g., peptides, having a reversal of both the peptide backbone direction and the amino acid chirality.

"Antifibrillogenic activity" includes the ability to block or prevent an amyloidogenic protein from forming fibrils, preferably by preventing it from adopting its β-pleated conformation, by disrupting protofilament interactions, and/or by interfering with the side chain interactions within the folded peptide, which are believed to be necessary for aggregation and fibril formation.

The term "cytoprotection" or "cytoprotective activity" includes molecules, e.g., peptides, having a the ability to protect cells from amyloid-induced toxicity.

The terms "antifibrillogenic agent" and "inhibitor of fibril formation" are used herein interchangeably.

The present invention provides new antifibrillogenic agents or inhibitors of fibril formation for controlling folding or deposition of amyloid proteins. The present invention also provides methods to prevent or delay the progression of diabetes and other amyloidosis disorders. The present invention further provides small peptides having inhibitory properties, and to provide agents capable of controlling IAPP aggregation and amyloid formation.

Antifibrillogenic agents of the invention for inhibiting amyloidosis and/or for cytoprotection are provided, including peptides such as ATQRLANFLVHSSSSNNF-GAILSSTN (SEQ ID NO. 1), ATQRLANFLVHSS (SEQ ID NO. 2), NVGSNTY (SEQ ID NO. 3) SSNNFGAILSSTN (SEQ ID NO. 4), ATQRLA (SEQ ID NO. 5), LANFLV (SEQ ID NO. 6), ANFLVH (SEQ ID NO. 7), NFLVHS (SEQ ID NO. 8), FLVHSS (SEQ ID NO. 9), SSNNFG (SEQ ID NO. 10), SNNFGA (SEQ ID NO. 11), NNFGAI (SEQ ID NO. 12), FGAILS (SEQ ID NO. 13), GAILSS (SEQ ID NO. 14), AILSST (SEQ ID NO. 15), ILSSTN (SEQ ID NO. 16), NVGSNT (SEQ ID NO. 17), and VGSNTY (SEQ ID NO. 18). Preferably, the peptide is SSNNFG (SEQ ID NO. 10), SNNFGA (SEQ ID NO. 11), GAILSS (SEQ ID NO. 14), AILSST (SEQ ID NO. 15), LANFLV (SEQ ID NO. 6) or ANFLVH (SEQ ID NO. 7).

In an embodiment of the invention, peptides for inhibiting amyloidosis and/or for cytoprotection are provided, wherein the peptide has a sequence selected from ATQRLA (SEQ ID NO. 5), LANFLV (SEQ ID NO. 6), ANFLVH (SEQ ID NO. 7), NFLVHS (SEQ ID NO. 8), FLVHSS (SEQ ID NO. 9), SSNNFG (SEQ ID NO. 10), SNNFGA (SEQ ID NO. 11), NNFGAI (SEQ ID NO. 12), FGAILS (SEQ ID NO. 13), GAILSS (SEQ ID NO. 14), AILSST (SEQ ID NO. 15), ILSSTN (SEQ ID NO. 16), NVGSNT (SEQ ID NO. 17), and VGSNTY (SEQ ID NO. 18).

Another embodiment of the invention relates to peptides for inhibiting amyloidosis and/or for cytoprotection, where the peptide binds to a sequence selected from ATQRLANFLVHSSSSNNFGAILSSTN (SEQ ID NO. 1), ATQRLANFLVHSS (SEQ ID NO. 2), NVGSNTY (SEQ ID NO. 3) SSNNFGAILSSTN (SEQ ID NO. 4), ATQRLA (SEQ ID NO. 5), LANFLV (SEQ ID NO. 6), ANFLVH (SEQ ID NO. 7), NFLVHS (SEQ ID NO. 8), FLVHSS (SEQ ID NO. 9), SSNNFG (SEQ ID NO. 10), SNNFGA (SEQ ID NO. 11), NNFGAI (SEQ ID NO. 12), FGAILS (SEQ ID NO. 13), GAILSS (SEQ ID NO. 14), AILSST (SEQ ID NO. 15), ILSSTN (SEQ ID NO. 16), NVGSNT (SEQ ID NO. 17), and VGSNTY (SEQ ID NO. 18), and upon peptide binding to the sequence, prevents fibril formation and amyloidosis.

The antifibrillogenic agents can be formulated in a composition for inhibiting amyloidosis and/or for cytoprotection, and include a therapeutically effective amount of antifibrillogenic agents of the invention in association with a pharmaceutically acceptable carrier.

Another embodiment of the invention relates to compounds for inhibiting amyloidosis and/or for cytoprotection which bind with a peptide as defined above. The compounds may be, e.g., an enzyme that binds to or controls the expression of the peptide, or an antibody that binds to the peptide. Such antibody may be specific for the peptide and may be either a monoclonal or polyclonal antibody.

Agents of the invention may be used for the ex vivo preparation of cells, e.g., in culture, suitable for transplantation into a mammal, e.g., islet cells, which cells are capable of forming amyloid deposits, wherein in the preparation of the cells to be transplanted, the cells are contacted with the antifibrillogenic agent. The antifibrillogenic agent causes a breakdown of amyloid deposits (the deposits having been formed by the cells prior to coming in contact with the antifibrillogenic agent).

The agents of the invention may advantageously be used in treating Type I diabetes patients post transplantation, wherein an antifibrillogenic agent is administered to a Type I diabetes patient for inhibiting, preventing and/or reducing amyloid deposit formation and amyloidosis. The antifibrillogenic agent may be administered in conjunction with insulin.

The antifibrillogenic agents may also be used in for inhibiting amyloidosis and/or for cytoprotection, wherein a therapeutically effective amount of the antifibrillogenic agent is administered to a subject, such that the antifibrillogenic agent prevents or reduces amyloid deposition. The antifibrillogenic agent may desirably be administered by cell therapy or gene therapy wherein the cells have been modified to produce and secrete the antifibrillogenic agent. Such cells may be modified ex vivo or in vivo.

The antifibrillogenic agents of the invention may also be used for imaging plaques, in which case the antifibrillogenic agents, e.g., peptides, are amyloid targeting imaging agents of the following formula:

(I)

where z is 0 or 1; $A_t$ is an antifibrillogenic agent of IAPP fibril formation as described herein; $A_{lnk}$ is a linker moiety; and $A_{lab}$ is a labeling moiety.

Labeling moiety $A_{lab}$ allows the amyloid targeting imaging agent, once at the target site in vivo, to be visualized by instrumentation such as CT, MRI, ultrasound, radioisotopic or fluorescence detection. The labeling moiety either modulates an externally applied energy or generates a detectable energy itself. The labeling moiety may be an echogenic substance in the case of an ultrasound contrast agent, a paramagnetic metal chelate in the case of an MRI contrast agent, a radioactive atom (e.g., radioactive fluorine) or a chelated radioactive metal ion (e.g., In-111) in the case of a radionuclide imaging agent, a radio-opaque chelate or compound (e.g., a polyiodinated aromatic) for an x-ray contrast agent, or a fluorescent or colored dye in the case of an optical imaging contrast agent. In one embodiment labeling moiety $A_{lab}$ may be a metal chelator. In an advantageous embodiment, $A_{lab}$ is a radionuclide (either a chelate of a metal ion or a single atom) or a paramagnetic metal ion chelate. According to one aspect of the invention, a labeled targeting molecule-chelator conjugate comprises a labeling moiety $A_{lab}$ (e.g., a radionuclide) attached directly to amyloid-targeting moiety $A_t$, therefore not requiring the use of a linker moiety.

Preferably, $A_{lab}$ includes a radionuclide selected from $^{99m}Tc$, $^{99}Tc$, $^{64}Cu$, $^{67}Cu$, $^{97}Ru$, $^{119}Pd$, $^{186}Re$, $^{188}Re$, $^{111}In$, $^{113m}In$, $^{153}Gd$, $^{90}Y$, 153Sm, $^{166}Ho$, $^{198}Au$, $^{199}Au$, $^{90}Sr$, $^{89}Sr$, $^{115}Rh$, $^{201}Tl$, $^{51}Cr$, $^{67}Ga$, $^{57}Co$, $^{60}Co$, $^{123}I$, $^{125}I$, $^{131}I$ or $^{18}F$.

As an imaging agent, $A_{lab}$ preferably includes a radionuclide selected from the group consisting of Tc and Re. More preferably, $A_{lab}$ is a metal chelate of a radioactive or paramagnetic metal ion.

In both AD and Type-II diabetes, amyloid plays a key role. The antifibrillogenic agents of the invention may be peptides, peptidomimetics, antibodies, or other compounds, that interact or interfere with either or both regions of the amyloidogenic peptide which are involved in amyloid formation, e.g. ATQRLANFLVHSS (SEQ ID NO. 2) and SSNNFGAILSSSTN (SEQ ID NO. 4) in the case of the IAPP peptide. The antifibrillogenic agents may also be enzymes that bind to or control the expression of the amyloidogenic peptide.

When the antifibrillogenic agents are peptides, all-[D] peptides, all-[L] peptides and peptides which are a mixture of [L] and [D] isomers are included. Without wishing to be limited to a particular theory or interpretation of how the invention operated, antifibrillogenic agents are believed to "interfere" with the amyloidogenic peptide by binding and disrupting the folding into the amyloidogenic β-sheet conformation, disrupting protofilament interactions, and/or interfering with the side chain interactions within the folded peptide, which are necessary for aggregation and fibril formation.

The antifibrillogenic agents of the invention may be peptides, which can be modified or substituted analogs. Some analogs also include unnatural amino acids or modifications of N or C terminal amino acids. Unnatural amino acids include D-amino acids, α,α-disubstituted amino acids, N-alkyl amino acids, lactic acid, 4-hydroxyproline, gamma-carboxyglutamate, ε-N,N,N-trimethyllysine, ε-N-acetyllysine, O-phosphoserine, N-acetylserine, N-formylmethionine, 3-methylhistidine, 5-hydroxylysine, Ω-N-methylarginine and isoaspartic acid.

The following terms are used to describe the sequence relationships between two or more polynucleotides: "substantial identity", "comparison window", "sequence identity", "percentage of sequence identity", and "reference sequence." A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 18 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 18 contiguous nucleotide positions wherein a polynucleotide sequence may be compared to a reference sequence of at least 18 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and aspargine-glutamine.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315–321 (1990); Kostelny et al., J. Immunol. 148, 1547–1553 (1992). Specific binding between two entities means an affinity of at least $10^6$, $10^7$, $10^8$, $10^9 M^{-1}$, or $10^{10} M^{-1}$. Affinities greater than $10^8$ M preferred.

A "pharmaceutical composition" refers to a chemical or biological composition suitable for administration to a mammalian individual. Such compositions may be specifically formulated for administration via one or more of a number of routes, including but not limited to, oral, parenteral, intravenous, intraarterial, subcutaneous, intranasal, sublingual, intraspinal, intracerebroventricular, and the like. A "pharmaceutical excipient" or a "pharmaceutically acceptable excipient" is a carrier, usually a liquid, in which an active therapeutic peptide is formulated. The excipient generally does not provide any pharmacological activity to the formulation, though it may provide chemical and/or biological stability, release characteristics, and the like. Exemplary formulations can be found, for example, in Remington's Pharmaceutical Sciences, $19_{th}$ Ed., Grennaro, A., Ed., 1995.

Such peptides, proteins or fragments, analogs and other amyloidogenic peptides may be synthesized by solid phase peptide synthesis or recombinant expression, according to standard methods well known in the art, or can be obtained from natural sources. Automatic peptide synthesizers may be used, and are commercially available from numerous manufacturers, such as Applied Biosystems (Perkin Elmer; Foster City, Calif.), and procedures for preparing synthetic peptides are known in the art.

Antifibrillogenic agents of the invention may also be derived from the peptides by substitution of one or more residues in the naturally occurring sequence. In another embodiment, the agents are peptidomimetics of the peptides. The agents may be modified by removing or inserting one or more amino acid residues, or by substituting one or more amino acid residues with other amino acids or non-amino acid fragments, such as thienylalanine, cyclohexylalanine and phenylglycine.

The antifibrillogenic agents, e.g., peptides, may be used to actively immunize a patient, so that patient after immunization will produce antibodies that will recognize the peptide sequence against which they have been raised. Alternatively, peptide antifibrillogenic agents of the invention can be used for producing antibodies to be administered to patients for passive immunization. The antibodies administered (in the case of a passive immunization) or the antibodies produced by the patients (in the case of an active immunization) will recognize a sequence on the IAPP corresponding to the sequence against which they have been raised, for inhibiting or reducing plaque formation.

In one illustrative embodiment, a series of small hexapeptides were generated to target an amyloidogenic region of hIAPP, residues 20–29, and their effects on β-sheet formation and fibrillar assembly were examined. Peptides SSNNFG (SEQ ID NO. 10) and SNNFGA (SEQ ID NO. 11), targeting the proximal end of hIAPP (20–29), were found to be strong inhibitors of β-sheet formation. Circular dichroism analysis revealed that even when used at a 1:1 molar ratio with IAPP, these peptides maintained hIAPP (1–37) in a random coil conformation. Negative stain electron microscopy revealed some semi-fibrillar aggregates, and the typical high density of IAPP fibrils was not seen. Peptide NFGAIL (SEQ ID NO. 19) from the internal section of hIAPP(20–29) was not inhibitory, but rather slightly enhanced fibril formation by hIAPP. As a result, the fibrillar morphology was more dense and complex than IAPP alone. Peptides GAILSST (SEQ ID NO. 20)and AILSST (SEQ ID NO. 15) from the distal portion of hIAPP 20–29 prevented the conformational change to β-sheet when used at higher molar ratios.

As an non-limiting illustration of the utility of the invention, the following types of amyloidosis are described in more detail below.

AA (Reactive) Amyloidosis

Generally, AA amyloidosis is a manifestation of a number of diseases that provoke a sustained acute phase response. Such diseases include chronic inflammatory disorders, chronic local or systemic microbial infections, and malignant neoplasms.

AA fibrils are generally composed of 8000 dalton fragments (AA peptide or protein) formed by proteolytic cleavage of serum amyloid A protein (apoSSA), a circulating apolipoprotein which is present in HDL complexes and which is synthesized in hepatocytes in response to such cytokines as IL-1, IL-6 and TNF. Deposition can be widespread in the body, with a preference for parenchymal organs. The spleen is usually a deposition site, and the kidneys may also be affected. Deposition is also common in the heart and gastrointestinal tract.

AA amyloid diseases include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia.

AL Amyloidoses

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia.

Fibrils of AL amyloid deposits are composed of monoclonal immunoglobulin light chains or fragments thereof. More specifically, the fragments are derived from the N-terminal region of the light chain (kappa or lambda) and contain all or part of the variable (VL) domain thereof. Deposits generally occur in the mesenchymal tissues, causing peripheral and autonomic neuropathy, carpal tunnel syndrome, macro glossia, restrictive cardiomyopathy, arthropathy of large joints, immune dyscrasias, myelomas, as well as occult dyscrasias. However, it should be noted that almost any tissue, particularly visceral organs such as the heart, may be involved.

Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 1 summarizes the fibril composition of exemplary forms of these disorders.

TABLE 1

| Fibril Peptide/Protein | Genetic variant | Clinical Syndrome |
|---|---|---|
| Transthyretin and fragments (ATTR) | Met30, many others | Familial amyloid polyneuropahty (FAP), (Mainly peripheral nerves) |
| Transthyretin and fragments (ATTR) | Thr45, Ala60, Ser84, Met111, Ile122 | Cardiac involvement predominant without neuropathy |
| N-terminal fragment of Apolipoprotein A1 (apoAI) | Arg26 | Familial amyloid polyneuropathy (FAP), (mainly peripheral nerves) |
| N-terminal fragment of Apoliproprotein A1 (AapoAI) | Arg26, Arg50, Arg 60, others | Ostertag-type, non-neuropathic (predominantly visceral involvement) |

TABLE 1-continued

| Fibril Peptide/Protein | Genetic variant | Clinical Syndrome |
|---|---|---|
| Lysozyme (Alys) | Thr56, His67 | Ostertag-type, non-neuropathic (predominantly visceral involvement) |
| Fibrogen ∀ chain fragment | Leu554, Val 526 | Cranial neuropathy with lattic corneal dystrophy |
| Gelsolin fragment (Agel) | Asn187, Tyr187 | Cranial neuropathy with lattice corneal dystrophy |
| Cystatin C fragment | Glu68 | Hereditary cerebral hemorrhage (cerebral amyloid angiopathy) - Icelandic type |
| β-amyloid protein (aβ) derived from Amyloid Precursor Protein (APP) | Gln693 | Hereditary cerebral hemorrhage (cerebral amyloid angiopathy) - Dutch type |
| β-amyloid protein (aβ) derived from Amyloid Precursor Protein (APP) | Ile717, Phe717, Gly717 | Familial Alzheimer's Disease |
| β-amyloid protein (aβ) derived from Amyloid Precursor Protein (APP) | Asn670, Leu671 | Familial Dementia - probably Alzheimer's Disease |
| Prion Protein (PrP) derived from Prp precursor protein 51–91 insert | Leu102, Val167, Asn178, Lys200 | Familial Creutzfeldt-Jakob disease; Gerstmann-Sträussler-Scheinker syndrome (hereditary spongiform encephalopathies, prion diseases) |
| AA derived from Serum amyloid A protein (ApoSSA) | | Familial Mediterranean fever, predominant renal involvement (autosomal recessive) |
| AA derived from Serum amyloid A protein (ApoSSA) | | Muckle-Wells syndrome, nephropathy, deafness, urticaria, limb pain |
| Unknown | | Cardiomyopathy with persistent atrial standstill |
| Unknown | | Cutaneous deposits (bullous, papular, pustulodermal) |

*Data derived from Tan & Pepys, Histopathology, 25(5): 403–414, 1994.

The data provided in Table 1 are exemplary and are not intended to limit the scope of the invention. For example, more than 40 separate point mutations in the transthyretin gene have been described, all of which give rise to clinically similar forms of familial amyloid polyneuropathy.

Transthyretin (TTR) is a 14 kilodalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients. Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art.

Persons having point mutations in the molecule apolipoprotein Al (e.g., Gly→Arg26; Trp 4→Arg50; Leu→4 Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form.

β-amyloid peptide ( Aβ) is a 39–43 amino acid peptide derived by proteolysis from a large protein known as Beta Amyloid Precursor protein (βAPP). Mutations in βAPP result in familial forms of Alzheimer's disease, Down's syndrome and/or senile dementia, characterized by cerebral deposition of plaques composed of Aβ fibrils and other components, which are described in further detail below. Known mutations in APP associated with Alzheimer's disease occur proximate to the cleavage sites of β or gamma-secretase, or within Aβ. For example, position 717 is proximate to the site of gamma-secretase cleavage of APP in its processing to Aβ, and positions 670/671 are proximate to the site of β-secretase cleavage. Mutations at any of these residues may result in Alzheimer's disease, presumably by causing an increase in the amount of the 42/43 amino acid form of Aβ generated from APP. The structure and sequence of Aβ peptides of various lengths are well known in the art. Such peptides can be made according to methods known in the art (e.g., Glenner and Wong, Biochem Biophys. Res. Comm. 129: 885–890, 1984; Glenner and Wong, Biochem Biophys. Res. Comm. 122: 1131–1135, 1984). In addition, various forms of the peptides are commercially available.

Synuclein is a synapse-associated protein that resembles an alipoprotein and is abundant in neuronal cytosol and presynaptic terminals. A peptide fragment derived from alpha-synuclein, termed NAC, is also a component of amyloid plaques of Alzheimer's disease. This component also serves as a target for immunologically-based treatments of the present invention, as detailed below.

Gelsolin is a calcium binding protein that binds to fragments and actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173–243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs.

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland. In at least some cases, patients with cerebral amyloid angiopathy (CAA) have been shown to have amyloid fibrils containing a non-mutant form of cystatin C in conjunction with beta protein.

Certain forms of prion disease are now considered to be inheritable, accounting for up to 15% of cases, which were previously thought to be predominantly infectious in nature (Baldwin, et al., in Research Advances in Alzheimer's Disease and Related Disorders, John Wiley and Sons, New York, 1995). In such prion disorders, patients develop plaques composed of abnormal isoforms of the normal prion protein (PrPSc). A predominant mutant isoform, PrPSc, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Sträussler-Scheinker syndrome (GSS), and fatal familial insomnia (FFI). (Baldwin, supra) Methods for extracting fibril peptides from scrapie fibrils, determining sequences and making such peptides are known in the art. For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate (Aβ2 microglobulin), joints and seminal vesicles.

Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. In fact, the incidence of sporadic Alzheimer's disease greatly exceeds forms shown to be hereditary. Fibril peptides forming these plaques are very similar to those described above, with reference to hereditary forms of Alzheimer's disease (AD).

Dialysis-related Amyloidosis

Plaques composed of β2 microglobulin (Aβ2M) fibrils commonly develop in patients receiving long term hemodialysis or peritoneal dialysis. β2 microglobulin is a 11.8 kilodalton polypeptide and is the light chain of Class I MHC antigens, which are present on all nucleated cells. Under normal circumstances, it is continuously shed from cell membranes and is normally filtered by the kidney. Failure of clearance, such as in the case of impaired renal function, leads to deposition in the kidney and other sites primarily in collagen-rich tissues of the joints). Unlike other fibril proteins, Aβ2M molecules are generally present in unfragmented form in the fibrils.

Hormone-derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), islet amyloid polypeptide (amylin; occurring in most patients with Type II diabetes), and atrial natriuretic peptide (isolated atrial amyloidosis). Sequences and structures of these proteins are well known in the art.

Miscellaneous Amyloidoses

There are a variety of other forms of amyloid disease that are normally manifest as localized deposits of amyloid. In general, these diseases are probably the result of the localized production and/or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid.

The invention, in a particular embodiment, is especially useful for treatment of diabetes, e.g., amyloid-related diabetes. The following description sets this forth in more detail.

Type II Diabetes and IAPP

Primary Structure of IAPP and Fibril Formation

There are three regions of human IAPP (hIAPP) that have the potential to form fibrils. In addition to the region 20–29, originally described as the amyloidogenic region (Betsholtz et al., FEBS Lett 251:261–264, 1989) and the recent report of hIAPP 30–37 forming fibrils (Nilsson & Raleigh, J Mol Biol 294:1375–1385, 1999), the present data indicate that hIAPP 8–20 also forms fibrils. These more recent findings suggest that 20–29 is not the only amyloidogenic region of the sequence. In addition, the fragment, rat IAPP 8–20, which has an arginine at position 18 but is otherwise homologous to hIAPP 8–20 formed fibrils in aqueous media.

While other studies have shown fragments of hIAPP to form fibrils rapidly in aqueous media, the data of the present invention have been obtained utilizing a preparation of hIAPP free of 'seeds' as the starting material (Higham et al., Eur J Biochem 267:4998–5004, 2000) rather than preparations of undefined solubility. Under these conditions, all peptide fragments were initially in random conformation when examined with CD and had no fibrillar structures present when examined by EM. This permitted examination of the effects of pH and counter ions on the change in peptide conformation from an unfolded state to the oligomerization and formation of fibrils. Previous studies have used HFIP to stabilize IAPP in artificial helical conformation or used seeds to generate conformational changes (Kayed et al., *J Mol Biol* 287:781–796, 1999), which may not reflect the situation in vivo. The use of preformed seeds could preclude the formation of initial aggregation stages important in the in vivo generation of amyloid.

The three adjacent domains of hIAPP that have amyloidogenic potential may have a role in intermolecular binding, oligomerization and fibril formation as well as interacting to form intramolecular β-sheets. This is the first report of fragments of rat IAPP (rat IAPP 8–20) forming fibrils. As the 30–37 region of rat IAPP is identical in amino acid structure to hIAPP and therefore capable of fibril formation, it could be predicted that these two β-strands interact and that rat IAPP should form fibrils. The lack of fibril formation from rat IAPP suggests that the proline substitutions at rat IAPP 25, 28, and 29 prevent β-strand formation in this region of the peptide; these proline substitutions not only inhibit intermolecular β-sheet formation and fibrils but also disrupt intramolecular structure that would lead to fibril formation.

The histidine residue at position 13 in Aβ is important for fibril assembly. Mutant forms of Aβ without histidine residues do not form structures larger than protofilaments. In rodents His 13 of Aβ is replaced with an arginine residue, in a similar way to the Arg 18His substitution that occurs in IAPP. This substitution is believed to contribute to the lack of Aβ amyloid in rodents.

Fibril formation of hIAPP 1–37 was independent of pH although the morphology differed. Counter-ions present in the buffer influenced the morphology as well as the rate of fibril formation. Human IAPP 1–37 formed fibrils at similar rates in water and 11 mM sodium-acetate and on a shorter time scale in 2 mM Tris buffer. This was accompanied by a conversion from random to β-sheet conformation as determined by CD analysis. Human IAPP 1–37 rapidly precipitated from 2 mM borate, citrate and phosphate buffers with a loss of CD signal. As the acetate and citrate buffers and the Tris and phosphate buffers were similar in ionic strength and matched for pH, the differences in effect were attributed to the charge or shape of the buffer ions. Citrate and phosphate are more densely charged than acetate and Tris respectively.

Binding of zinc to the histidine residue in the Aβ peptide has been proposed as an important factor for fibril assembly. The role of zinc in IAPP fibril formation was examined since a high concentration of zinc is present in the β-cell secretory granule that could influence the folding of IAPP. The presence of His 18 was shown not to be essential as rat IAPP 8–20 also formed fibrils. However, in the presence of zinc, fragments 18–29 and 20–29 formed longer more loosely packed fibrils. These results suggest that zinc is able to affect the packing of peptide fragments into protofilaments and assembly of protofilaments into fibrils independently of any interaction it may have with His18. The highly charged zinc ion could interact with hydrophobic residues preventing lateral aggregation.

Secondary Structure Propensities of hIAPP

Due to the difficulty in obtaining a soluble state of hIAPP at high concentration, a crystal structure has not been determined. Previous studies examining secondary structure predictions have produced various potential conformations for hIAPP (Hubbard et al., *Biochem J* 275:785–788, 1991; Saldanha & Mahadevan, *Protein Eng* 4:539–544, 1991).

Structure predictions indicate that an alpha helix should be present at the N-terminus of hIAPP. However, the CD data in this study indicate that hIAPP is usually found either in a random coil state, a β-sheet, or precipitated from solution (Higham et al., *Febs Lett* 470:55-60, 2000). Only in the presence of helix promoting solvents (TFE, HFIP) does it exhibit alpha helical nature (Higham et al., *Febs Lett* 470:55–60, 2000). This suggests either that hIAPP, in vitro, does not retain its native structure or that hIAPP is unstructured and, under appropriate conditions, assumes a β-sheet structure more easily than other conformations. Alternatively, hIAPP in vivo could exist as a random coil structure and circulate bound to a carrier to maintain stability. Although the secondary structures predicted by algorithms are based on known structures, they cannot predict whether a molecular conformation is kinetically accessible and therefore possible to attain in vitro or in vivo.

The conformations determined separately for different domains of the peptide may not represent that existing in the intact molecule since fragmentation removes tertiary contacts and fibril formation of separate fragments may occur under conditions where the full-length sequence does not form fibrils. Rat IAPP 8–20 will form fibrils but the full-length rat IAPP does not. However, despite the limitations of both secondary structure predictions and the difficulties of inference of structure from fragments these methods can be used to model peptides.

Proposal of a Model for hIAPP Fibril Formation

The presence of two/three β-strands in the hIAPP sequence suggests that a small β-sheet is at the core of the monomeric structure. This could be stabilized by side chain hydrogen bonding between the uncharged polar side chains of asparagine and/or glutamine residues.

Fibril formation of hIAPP is independent of pH and counter ions and is driven by hydrophobic interactions. In the hIAPP sequence, 11 of 37 residues are hydrophobic. Increased hydrophobicity during the initial stages of hIAPP fibril formation has been demonstrated (Kayed et al., *J Mol Biol* 287:781–796, 1999) suggesting that protofilament and fibril assembly exposes hydrophobic groups. Uncharged polar residues such as glutamine, serine, asparagine and threonine participate in side chain hydrogen bonding. Griffiths et al. (Griffiths et al., *Journal of the American Chemical Society* 12:3539–354, 1995) suggested that residues 24–27 form a highly ordered antiparallel β-sheet structure when examined as a 20–29 fragment.

A new amyloidogenic domain of hIAPP has been identified using a series of overlapping peptide fragments. These results provide a new insight into molecular sequences important in amyloid fibril formation. Although the hIAPP 20–29 domain is clearly important, it is unlikely to act in isolation and other IAPP regions must contribute to formation/stabilization of the β-sheet conformation and the accompanying aggregation and fibril formation.

The results presented herein show that there are at least two regions of IAPP involved in fibril formation, one β-pleated sheet region (IAPP 20–29) and one region of previously unknown function (IAPP 8–20). The antifibrillogenic agents of the present invention can act by interacting or interfering with either or both regions.

The fibril forming ability of hIAPP was pH insensitive, suggesting that the transition of IAPP in vivo from the β-cell secretory granule (pH 5.5) to the extracellular space (pH 7.4) does not have a significant effect on the conformation of the peptide. It is more likely that changes in the granule components or in the extracellular environment, which are unique to Type II diabetes, allow fibril formation to occur. The β-cell granule contains more than 30 identified proteins and has high concentrations of both zinc and calcium. Intracellular molecular crowding could be essential for maintenance of hIAPP in its native conformation or inhibition of aggregation. Changes which promote 'seeding' of amyloidogenic fragments or conformational rearrangements of intact hIAPP 1–37 initiate the progressive deposition of secreted IAPP as amyloid deposits and destruction of insulin-secreting cells. Similarly, crowding effects in the extracellular space in the early stages of Type II diabetes due to hypersecretion from the β-cells could result in increased concentration of hIAPP and aggregation leading to fibril formation.

The ultimate goal in the present invention is to control the disease process to prevent, delay or reverse the progression of Alzheimer's disease, diabetes or other amyloidosis disorders. Non-limiting examples of amyloidosis disorders are cerebral angiopathy, secondary amyloidosis, familial Mediterranean fever, Muckle-Wells syndrome, primary amyloidosis, familial amyloid polyneuropathy, hereditary cerebral hemorrhage, chronic hemodialysis-associated amyloidosis, and prion disorders such as Creutzfeld-Jacob disease and Gertsmann-Straussler-Scheinker syndrome.

In accordance with the invention, a series of IAPP-derived peptide fragments has been identified. These fragments have the ability to bind to the full-length protein and prevent normal folding and amyloid fibril formation. The activity of these inhibitors has been assessed, as detailed hereinbelow, using a series of biophysical techniques that include protein spectroscopy, fluorescence assays and electron microscopy.

The following section describes particularly active anti-fibrillogenic agents that have been noted by the inventors, which have been refined using mutational analysis to identify key residues and to define the smallest active domain.

EXEMPLIFICATION/EXPERIMENTAL

FIG. 1 illustrates the sequence of the amyloid-β (Aβ) peptide and its proposed structural domains. A peptide-based approach similar to that used for Aβ (Tjernberg, et al, *J Biol Chem* 272:12601–12605, 1997) has been used for targeting two key domains in IAPP initially ranging from the 8–20 and 20–29 sequences as shown in FIG. 2. These peptides, as has been shown for Aβ peptides, are able to bind to the full-length IAPP peptide and alter fibrillogenesis. The peptides disrupt fibrillogenesis by disrupting the folding into the amyloidogenic β-sheet conformation, disrupting protofilament interactions, and/or interfering with side chain interactions within the folded IAPP, which are necessary for aggregation and fibril formation. The peptides that have been examined (shown in FIG. 2) were small, synthetic hexapeptides that correspond to the principal sequence domains of IAPP. These peptides were evaluated in vitro and the most active sequences were identified. The in vitro assays included: Circular Dichroism (CD), to look at changes in folding of the amyloidogenic β-sheet; negative stain electron microscopy (EM) to examine changes in fibril morphology and relative density; and ThT fluorescence assay which provides a quantitative assessment of fibril formation.

In the present application, the following experimental procedures have been used.

Peptide Synthesis and Supply

Synthetic human IAPP (1–37) was purchased from BACHEM (Torrence, Calif.), synthetic peptides spanning the region from IAPP 8 to 20 and 19–31 (FIG. 3) were synthesized by the Peptide Synthesis Laboratory at the University of Toronto using standard FMOC (Fluoroenylmethoxycarbonyl) based solid phase peptide synthesis methodology. The peptides were purified by reverse phase HPLC using water/acetonitrile mixtures buffered with 0. 1% trifluoroacetic acid, on a POROS 20R2 column. The synthetic peptides were solubilized in 110% HFIP (1 mg/ml), filtered (0.2 μm), aliquotted and lyophilized (Higham, C E., et al., *FEBS Lett.* 470: 55–60, 2000). Aliquots were reconstituted as required in 20 mM sodium acetate buffer pH 6.5.

Circular Dichroism Spectroscopy (CD)

CD was used to measure the peptide conformational changes associated with fibril formation. CD experiments were carried out at room temperature, and spectra (average of 5 scans) were collected using a Jasco J720 spectropolarimeter and quartz cuvettes with a path length of 1 mm.

Transmission Electron Microscopy (TEM)

TEM was used for structural analysis of in vitro assembled fibrils. Aliquots (4 μl) were applied to pioloform and carbon coated grids. The samples were incubated on the grids for 3 minutes at room temperature, excess material blotted off and stained with 1% phosphotungstic acid (PTA). Excess PTA was blotted off and the sample was left to air dry. All samples were examined using a Hitachi 7000 electron microscope with an accelerating voltage of 75 kV.

Sedimentation Assay

Aliquots of lyophilized hIAPP 1–37 were dissolved in 20 mM acetate buffer (pH 6.5) to 11 μM and incubated in a total volume of 500 μl at room temperature. Tyrosine emission spectra were collected (emission wavelength 275 nm) on a Beckman DU530 spectrophotometer for each sample at time 0. Following a 24 hour incubation at room temperature, the soluble and aggregated peptides in each sample were separated by centrifugation at 16,000 g for 20 minutes, and the emission spectra were measured on the soluble fractions. The samples were then vortexed to resuspend the entire contents of each tube, and were incubated for an additional 24 hours. This process was repeated for a total of 72 hours of incubation. For co-incubation experiments, hIAPP was incubated with a 10 fold excess concentration (110 μM) of the inhibitory peptides SNNFGA (SEQ ID NO. 11), and GAILSS (SEQ ID NO. 14).

In preliminary work the series of peptides were synthesized from the 20–29 domain and examined, via CD, EM and ThT fluorescence, at two molar ratios (1:10 and 1:20) in comparison to the full-length IAPP residues 1–37. The following data (FIGS. 5A to 5D, 6A to 6C and 7A to 7B) were obtained.

Results

Figure 3B:
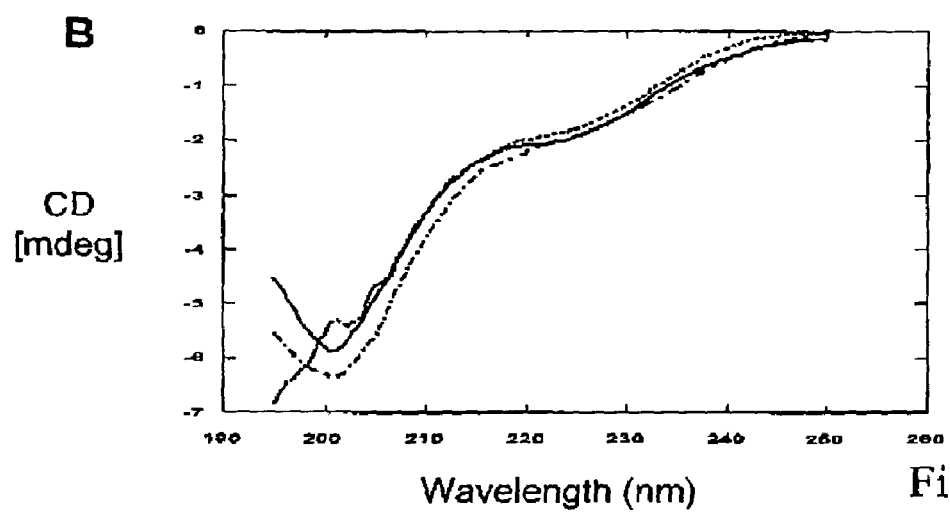
Figure 3C:
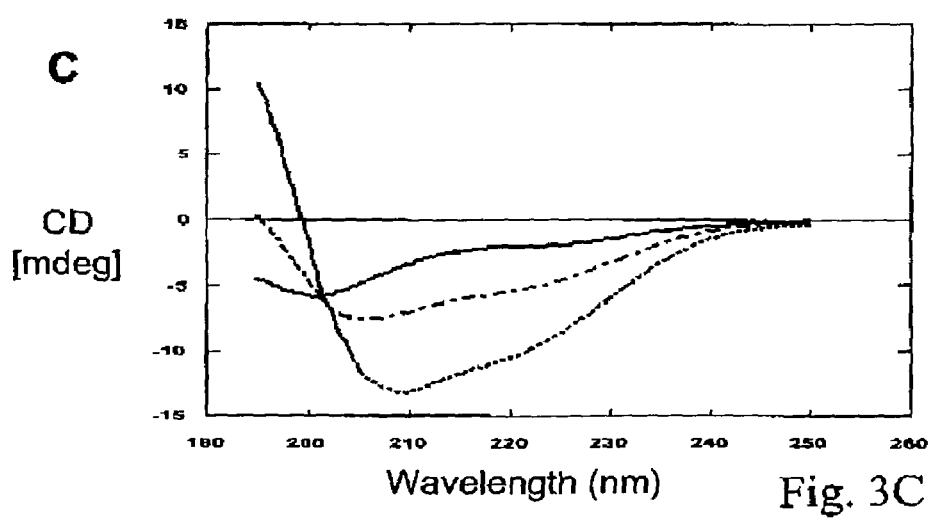

When dissolved in 20 mM acetate buffer, full-length hIAPP exhibits a characteristic CD spectra for random coil structure. A conformational change from random coil to β-sheet was measured following a 48-hour incubation at room temperature (FIG. 3A). The addition of peptides SSNNFG (SEQ ID NO. 10), SNNFGA (SEQ ID NO. 11), NNFGAI (SEQ ID NO. 12), FGAILS (SEQ ID NO. 13), GAILSS (SEQ ID NO. 14), AILSST (SEQ ID NO. 15), and ILSSTN (SEQ ID NO. 16) at a 1:10 (dashed line) or 1:20 (dotted line) molar ratio did not cause an attenuation of signal at time 0 demonstrating that these peptides had no effect on the initial random structure of IAPP (FIG. 3B) thus suggesting that these peptides did not cause an attenuation of signal due to precipitation of IAPP following aggregation. Time 0 data for SSNNFG (SEQ ID NO. 10) is shown. In contrast to the other peptides, incubation of IAPP with a 10 fold excess of NFGAIL (SEQ ID NO. 19) induced as seen in FIG. 3C a conformational change at time 0 (dashed line), and a 20 fold excess (dotted line) had a more pronounced effect by producing a conformational change from random coil to β-sheet. Therefore, the peptide NFGAIL (SEQ ID NO. 19) caused an immediate change in CD spectra at time 0 from a random coil structure to an intermediate conformation between random coil and β-sheet. This data suggests that rather than having inhibitory properties, peptide NFGAIL (SEQ ID NO. 19) may actually enhance IAPP fibril formation, and that the region contained within this peptide sequence may be intrinsic to the amyloidogenic properties of IAPP. In FIG. 3A, hIAPP (1–37) incubated in 20 mM acetate buffer pH 6.5 appeared as a random coil at time 0 (solid line). Following a 48-hour incubation the random coil structure underwent a transition to a β-sheet (dashed line).

Figure 4A:
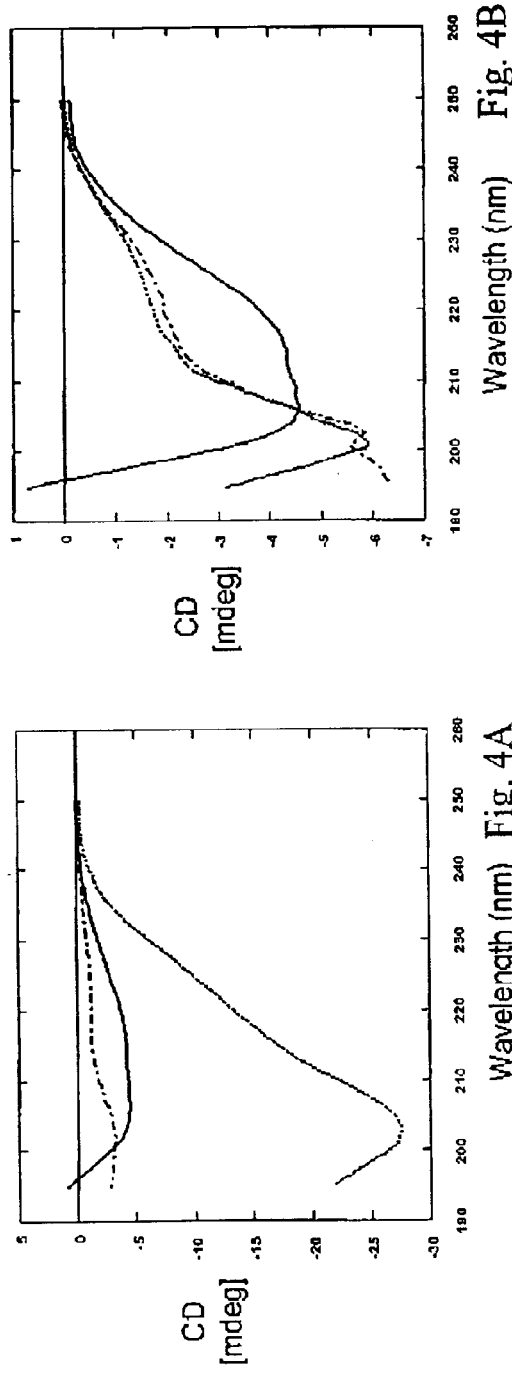
FIGS. 4A to 4D illustrate changes in the conformation of IAPP following incubation with peptide fragments.
Figure 4B:
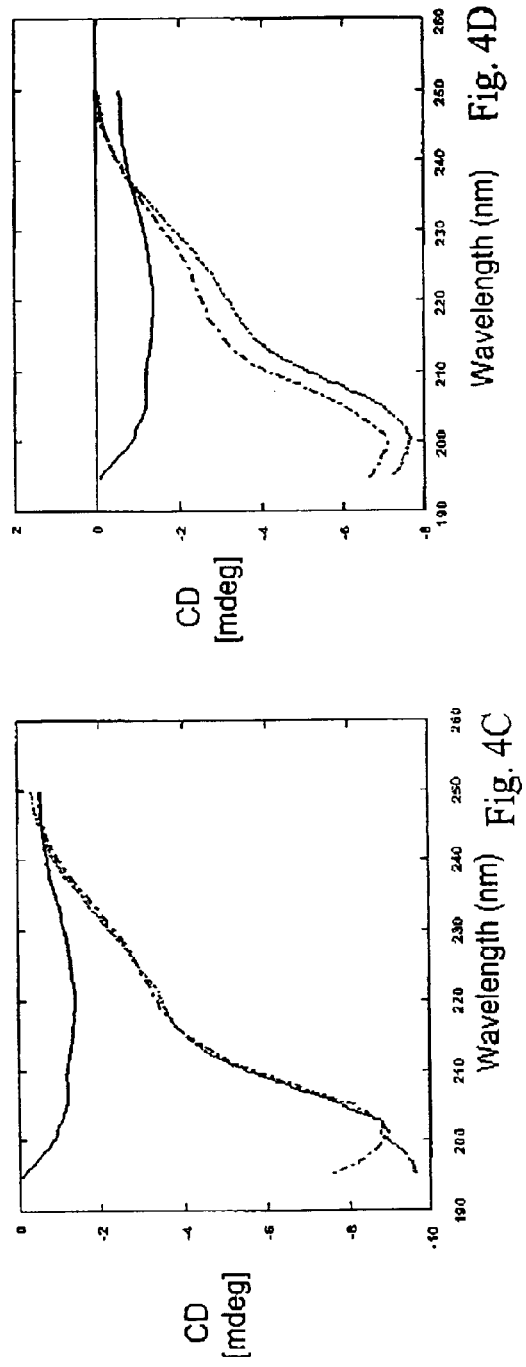

Changes in the CD spectra for IAPP were examined following prolonged incubation with individual hexapeptides. IAPP was incubated with each of the peptides shown in FIGS. 4A to 4D. CD spectra were recorded for 24–72 hours. Previous studies have demonstrated that IAPP fibrillogenesis can occur over a range of pH values from acidic to neutral pH. Therefore, only one condition (pH 6.5), midway between the acidic pH of the β cell secretory granule (pH 5.5) and the extracellular space (pH 7.4) was chosen for these experiments. For the purpose of brevity, the data from a select few peptides will be shown using a 48-hour incubation as a standard incubation period. Peptides NNFGAI (SEQ ID NO. 12), FGAILS (SEQ ID NO. 13) and ILSSTN (SEQ ID NO. 16) had little effect on the ability of hIAPP (1–37) to form a β-sheet (FIG. 4A). The CD spectra indicated precipitation of the peptide from solution in the presence of a 10-fold molar excess of NNFGAI (SEQ ID NO. 12). Incubation of IAPP with a 10 fold molar excess of NNFGAI (SEQ ID NO. 12) had thus no effect on aggregation or precipitation of hIAPP (dashed line). In fact, in FIG. 4A, certain peptides such as NNFGAI (SEQ ID NO. 12) had little effect on the ability of IAPP (1–37) to form a β-sheet following a 48 hour incubation. CD spectra for IAPP indicated precipitation of the peptide from solution following the aggregation of the peptide (solid line). A 20-fold molar excess of this peptide was required to maintain IAPP in a random conformation (dotted line) suggesting that NNFGAI (SEQ ID NO. 12) has little, if any, inhibitory properties (FIG. 4A). Peptides SSNNFG (SEQ ID NO. 10) and SNNFGA (SEQ ID NO. 11) were capable of maintaining IAPP in a random conformation. Both peptides were effective inhibitors even when used at low concentrations (FIG. 4B). Peptides GAILSS (SEQ ID NO. 14) and AILSST (SEQ ID NO. 15) were able to prevent the attenuation of signal due to precipitation of IAPP (FIGS. 4C and 4D).

Figure 4C:
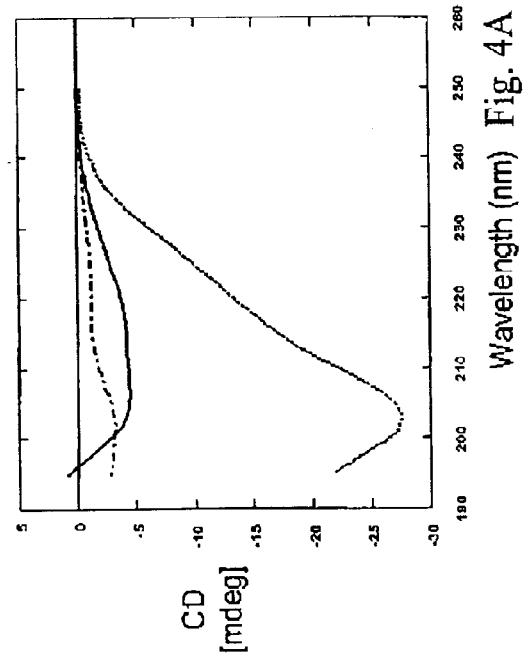
Figure 4D:
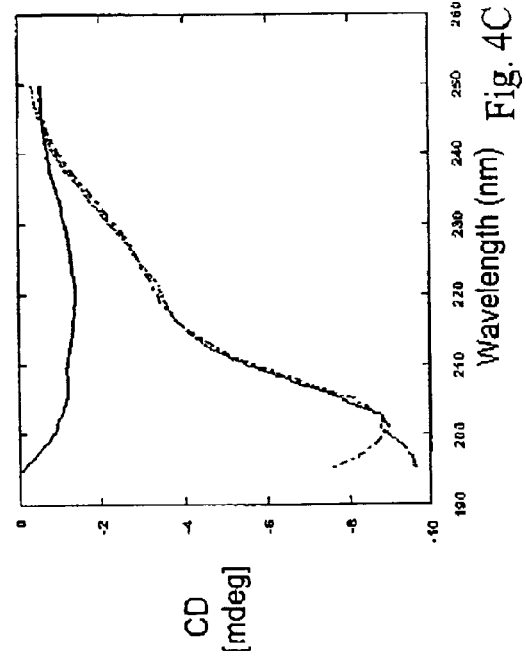

In FIGS. 4C and 4D, peptides GAILSS (SEQ ID NO. 14) and AILSST (SEQ ID NO. 15) were both very strong inhibitors of IAPP β-sheet transition and the accompanying aggregation when used at either a 1:20 (dotted line) or a 1:10 (dashed line) molar ratio.

Figure 5A:
FIGS. 5A to 5D illustrate electron micrographs of IAPP following 48 hour incubation with inhibitory peptides.
Figure 5B:
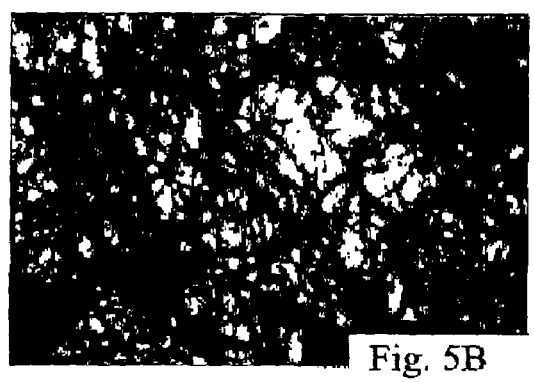
Figure 5C:
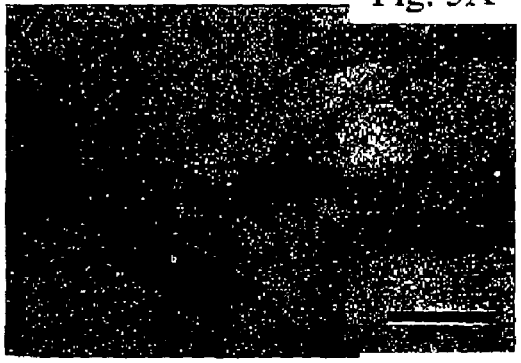
Figure 5D:
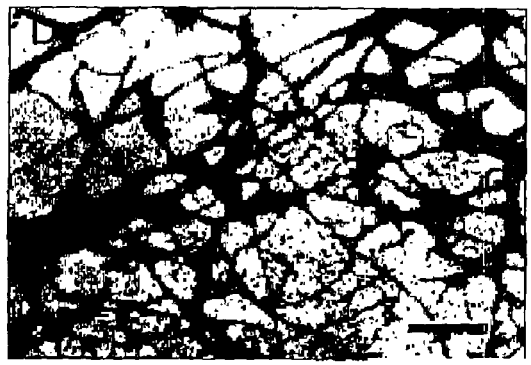

Following incubation with the hexapeptides, the morphology of IAPP was examined by negative stain electron microscopy. In FIG. 5A the inhibitory peptide is the full-length IAPP (1–37) fibrils. Full-length hIAPP (1–37) forms fibrillar assemblies composed of multiple protofibrils (FIG. 5A). These structures are defined by the dense collections of IAPP fibrils having a mesh-like morphology. The addition of peptides NNFGAI (SEQ ID NO. 12), NFGAIL (SEQ ID NO. 19), and FGAILS (SEQ ID NO. 13) had no effect on the morphology of IAPP fibrillar aggregates. The peptide NFGAIL (SEQ ID NO. 19) (20 fold molar excess) appeared to enhance IAPP aggregation leading to a more complex and denser mesh of fibrils (FIG. 5B). In FIGS. 5C and 5D, the inhibitory peptides GAILSS (SEQ ID NO. 14) (FIG. 5C) and SNNFGA (SEQ ID NO. 11) (FIG. 5D) caused a disruption in IAPP fibrillar structure. Incubation of IAPP with a 10- or 20-fold molar excess of either GAILSS (SEQ ID NO. 14) or SNNFGA (SEQ ID NO. 11) did not completely prevent fibril formation. CD analysis demonstrated that the majority of IAPP in these samples was maintained in a random conformation when incubated in the presence of these inhibitors. The hIAPP fibrillar aggregates that did form when incubated with these peptides were altered in appearance (FIGS. 5C and 5D). The fibrils were less numerous and more threadlike. In addition, the typical dense aggregation was not observed, suggesting that the aggregates that managed to form did not act as nuclei for additional fibrillogenesis. In FIGS. 5A, 5B and 5D, the scale bars represent 1 μm, whereas in FIG. 5C, the scale bar represents 0.5 μm.

Figure 6A:
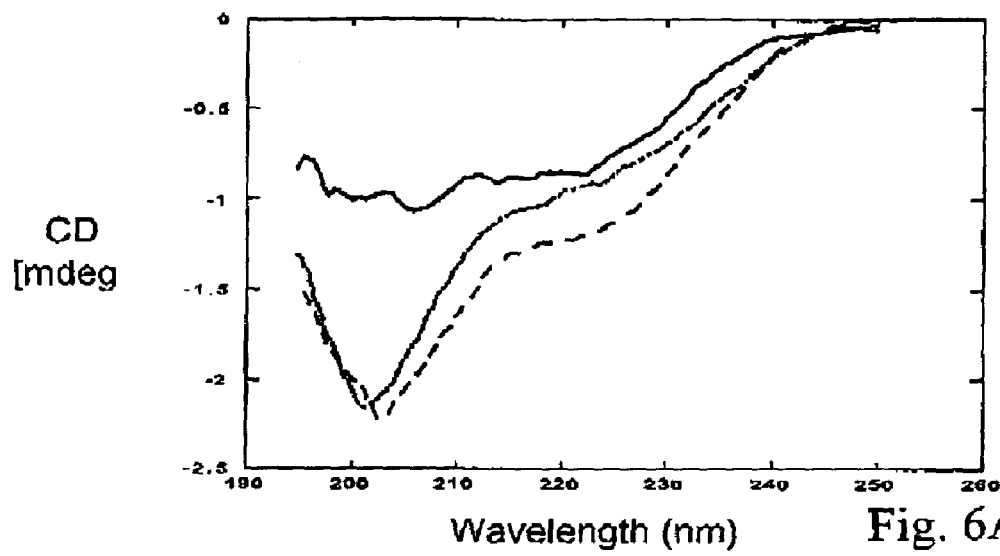
FIGS. 6A to 6C illustrate conformational changes in IAPP as a function of inhibitor concentration.
Figure 6B:
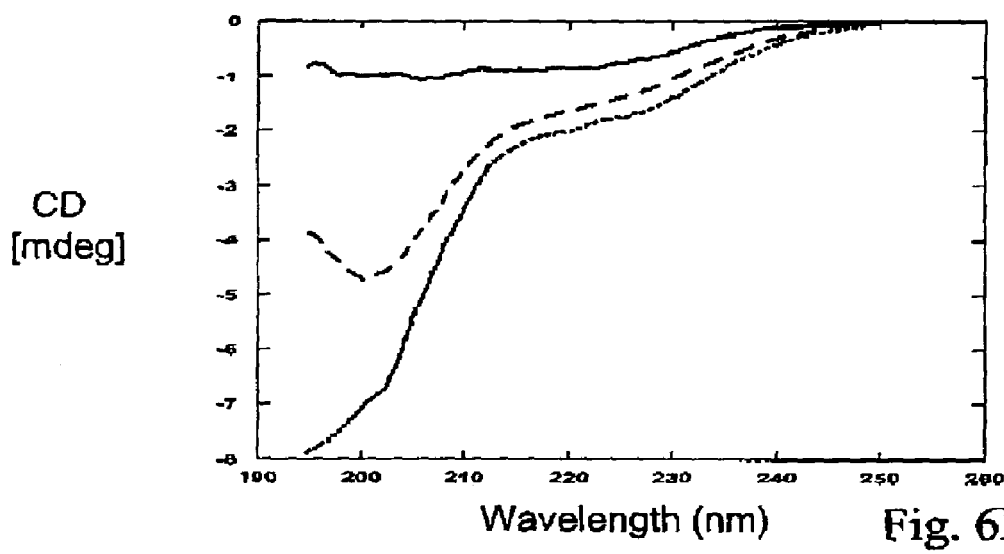
Figure 6C:
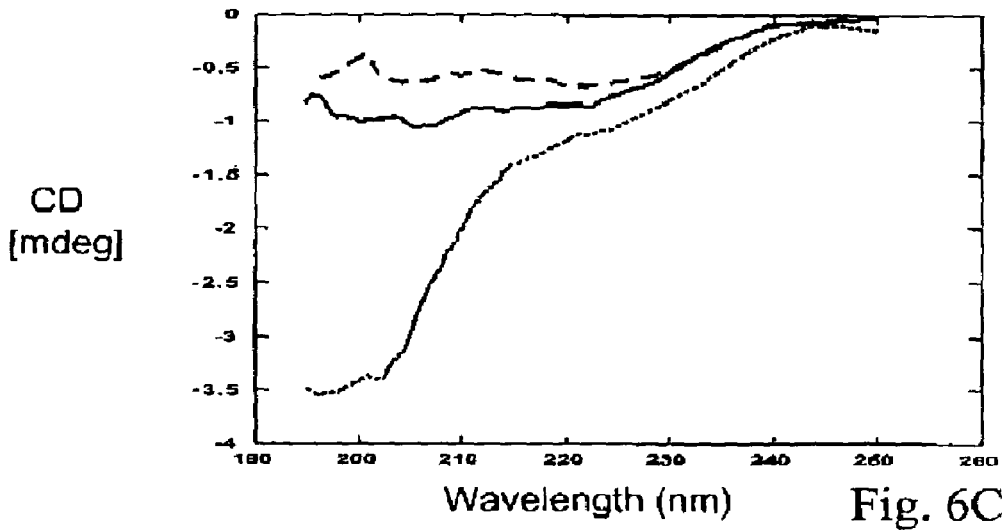

As a result of CD spectral analysis, peptides SNNFGA (SEQ ID NO. 11), GAILSS (SEQ ID NO. 14), and AILSST (SEQ ID NO. 15), demonstrated the greatest inhibition of IAPP fibril formation. Therefore, further experiments were carried out to determine their relative inhibition at lower concentrations. Peptide SNNFGA (SEQ ID NO. 1l) retained its inhibitory properties when reduced to a 5-fold molar ratio (dotted line) or an equimolar concentration (dashed line) with IAPP. This was demonstrated by its ability to prevent the IAPP β-sheet conformational change from a random coil (FIG. 6A). Peptide GAILSS (SEQ ID NO. 14) was also a very strong inhibitor when used at reduced concentrations (FIG. 6B). GAILSS (SEQ ID NO. 14) showed properties similar to those of SNNFGA (SEQ ID NO. 11), in that it was also equally inhibitory when the concentration was reduced to either a 5-fold excess (dotted line) or a 1:1 molar ratio (dashed line). In contrast, the peptide AILSST (SEQ ID NO. 15) was able to maintain hIAPP as a random coil peptide when used at a 5-fold molar excess (dotted line), but was no longer inhibitory when the concentration was further lowered to a 1:1 molar ratio (dashed line)(FIG. 6C). In agreement with these data, IAPP fibril morphology was altered even when inhibitor concentrations were reduced (FIGS. 6A to 6C). Peptides GAILSS (SEQ ID NO. 14) and SSNFGA (SEQ ID NO. 21) were both effective inhibitors of normal IAPP fibrillar aggregation. The fibrillar structures that infrequently form in the presence of these peptides were elongated and ribbon-like, and they did not assemble into the dense mesh-like structures seen for IAPP alone.

Sedimentation assays were performed to confirm the results from CD and electron microscopic analysis (FIGS. 7A and 7B) on the ability of peptides SNNFGA (SEQ ID NO. 11) and GAILSS (SEQ ID NO. 14) to inhibit IAPP fibril formation. hIAPP (11 μM) was incubated for a period of 72 hours in 20 mM acetate buffer alone, or with a 10 fold excess (110 μM) of the peptides.

Figure 7B:
FIGS. 7A and 7B illustrate electron micrographs of IAPP fibrils after incubation with GAILSS (SEQ ID NO. 14) (FIG. 7A), or SNNFGA (SEQ ID NO. 11) (FIG. 7B)
Figure 7A:
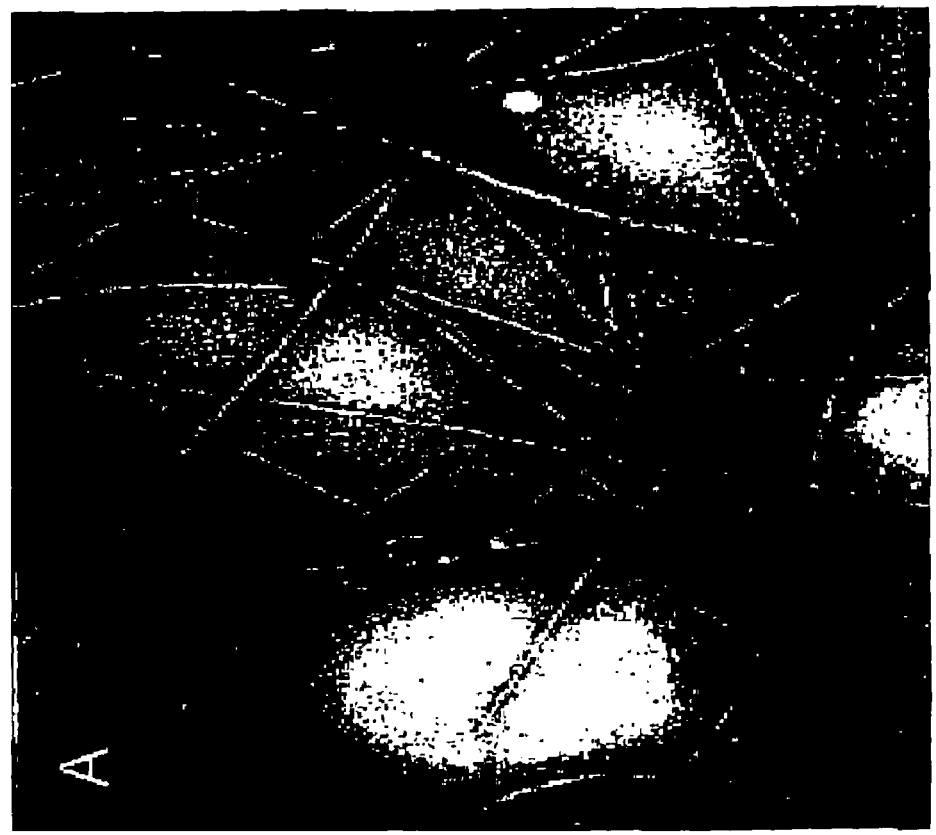

In FIGS. 7A and 7B, IAPP was incubated for 48 hours with peptides at a concentration of 1:1 (GAILSS (SEQ ID NO. 14)) or 1:5 (SNNFGA (SEQ ID NO. 11)) respectively. In FIG. 7A, the scale bar represents 0.5 μm, whereas the scale bar in FIG. 7B represents 1 μm.

Figure 8:
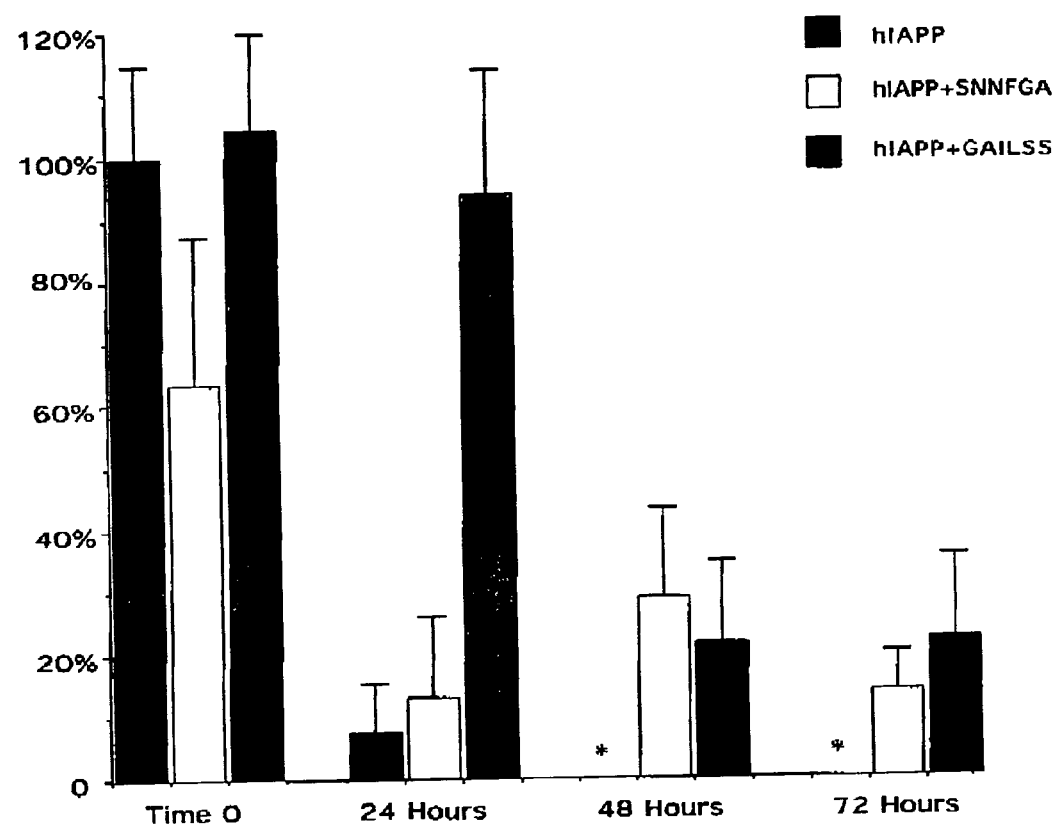
FIG. 8 illustrates a sedimentation assay to determine the relative amount of soluble and insoluble IAPP.
Figure 9A:
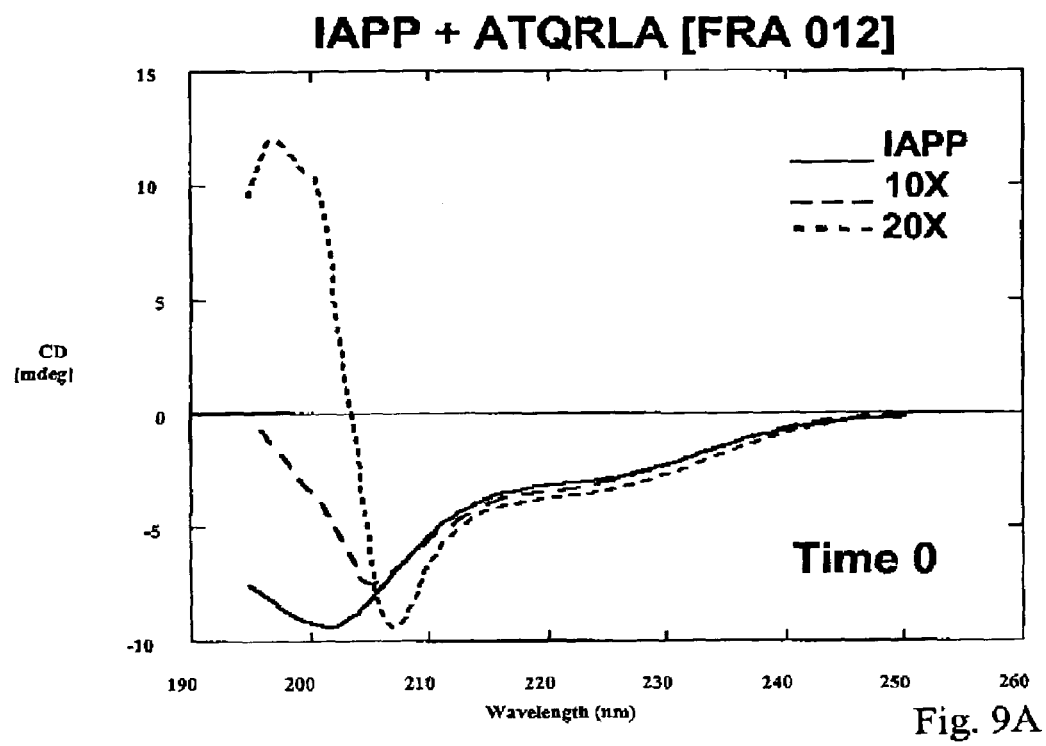
FIGS. 9A and 9B illustrate changes in the conformation of IAPP following incubation with FRA-012 peptide.
Figure 9B:
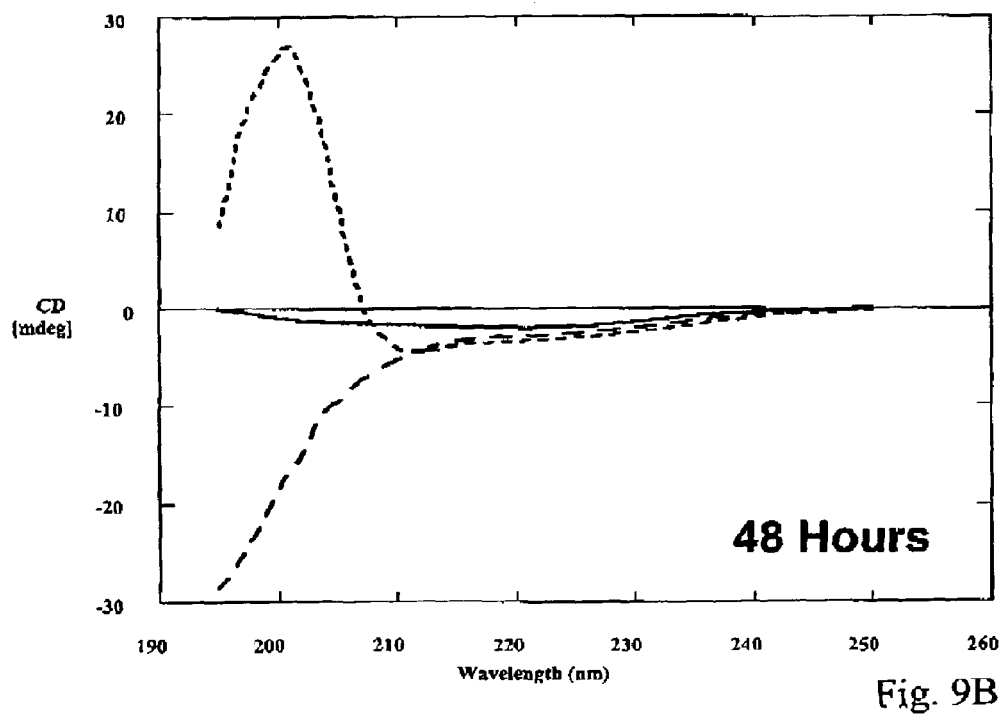
Figure 10A:
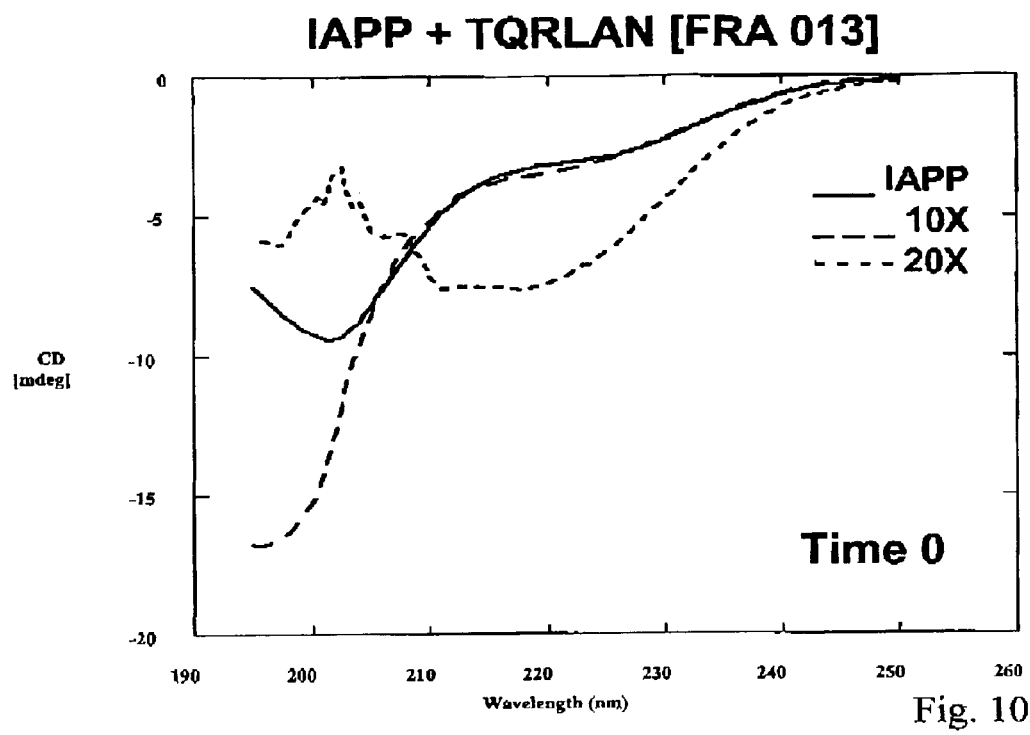
FIGS. 10A and 10B illustrate changes in the conformation of IAPP following incubation with FRA-013 peptide.
Figure 10B:
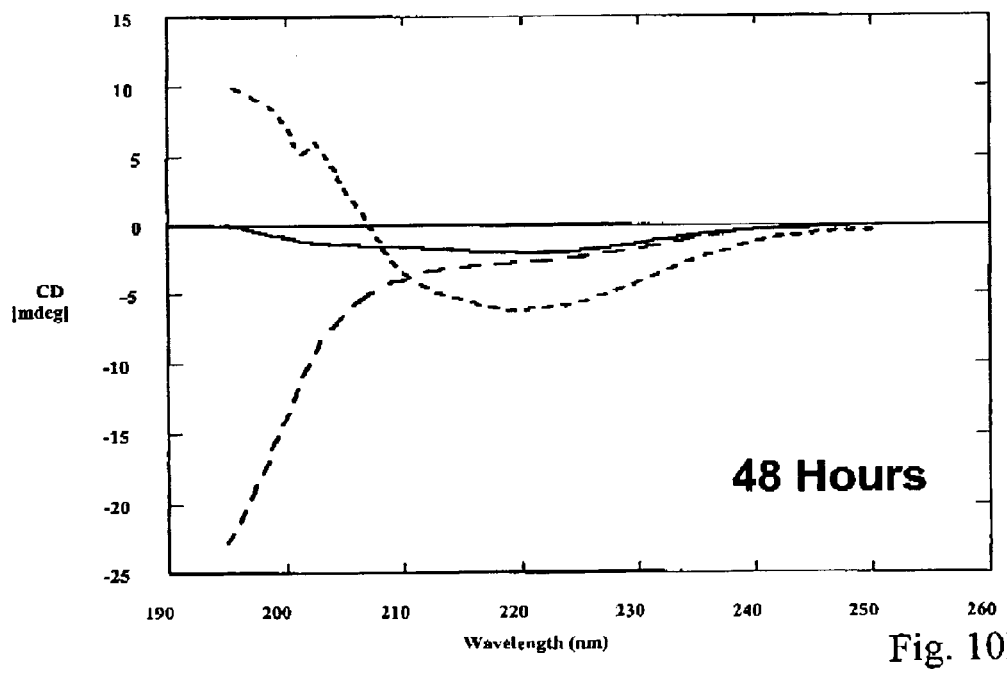
Figure 11A:
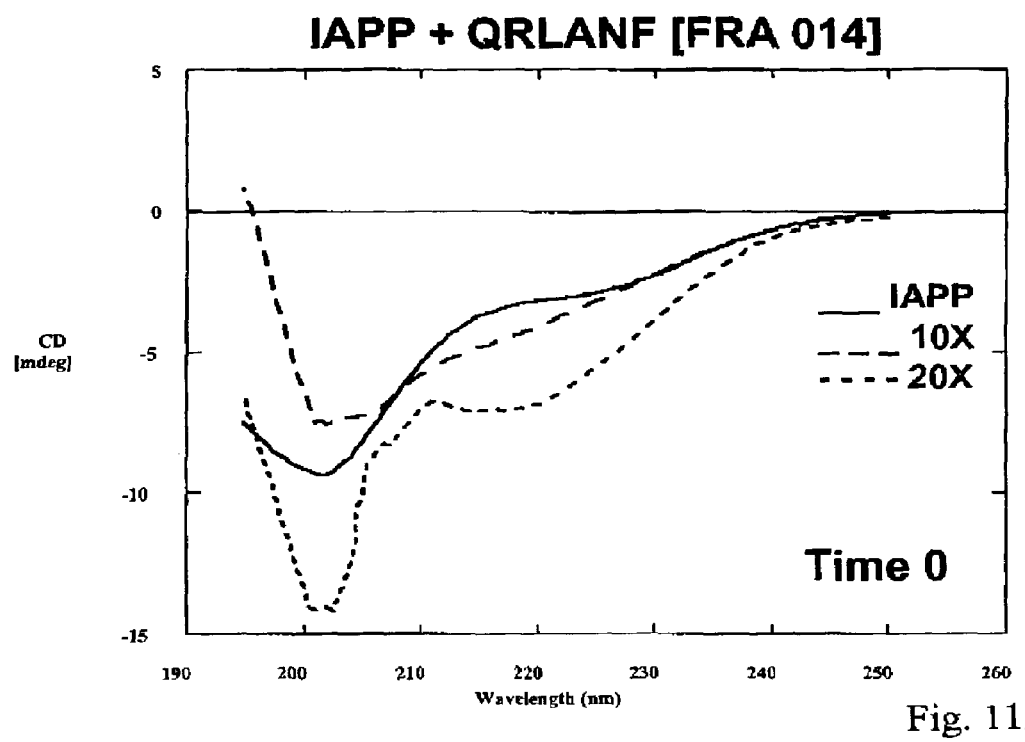
FIGS. 11A and 11B illustrate changes in the conformation of IAPP following incubation with FRA-014 peptide.
Figure 11B:
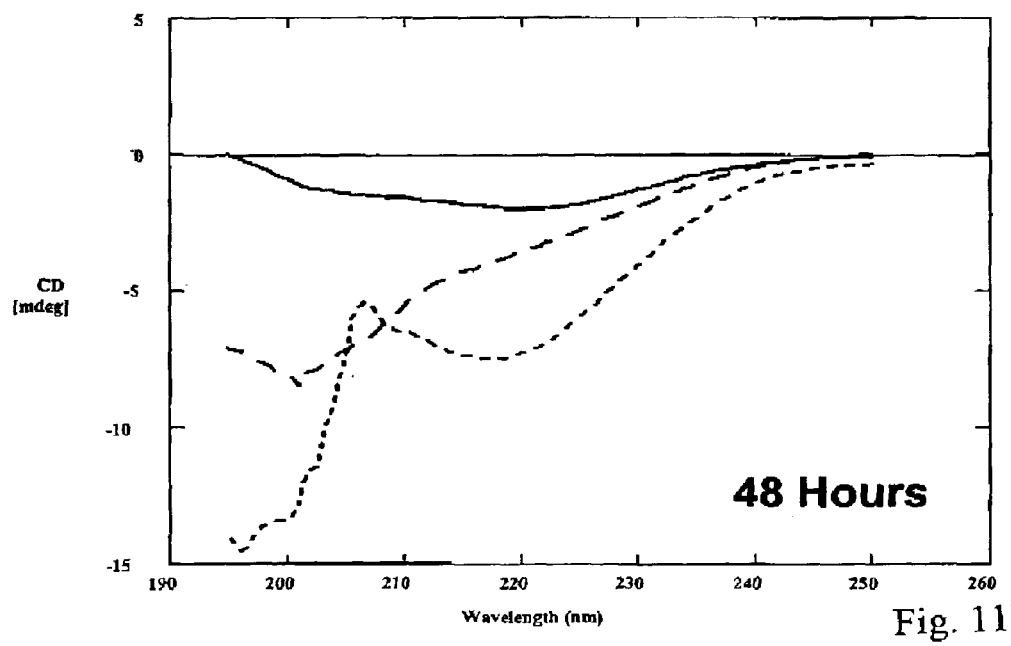
Figure 12A:
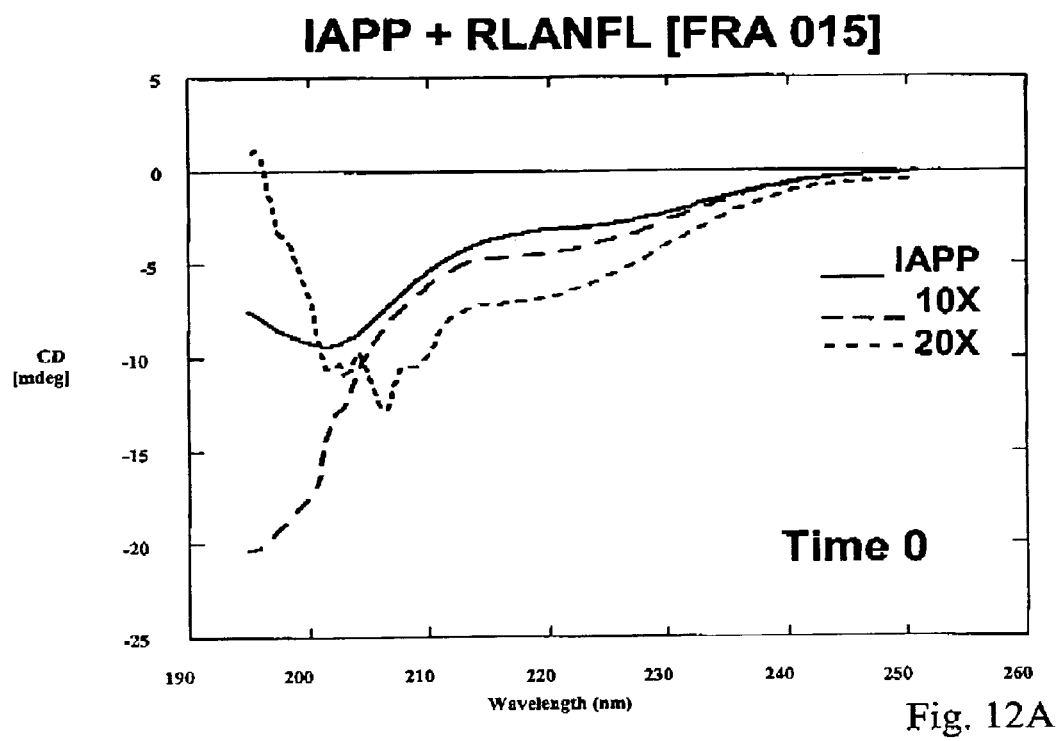
FIGS. 12A and 12B illustrate changes in the conformation of IAPP following incubation with FRA-015 peptide.
Figure 12B:
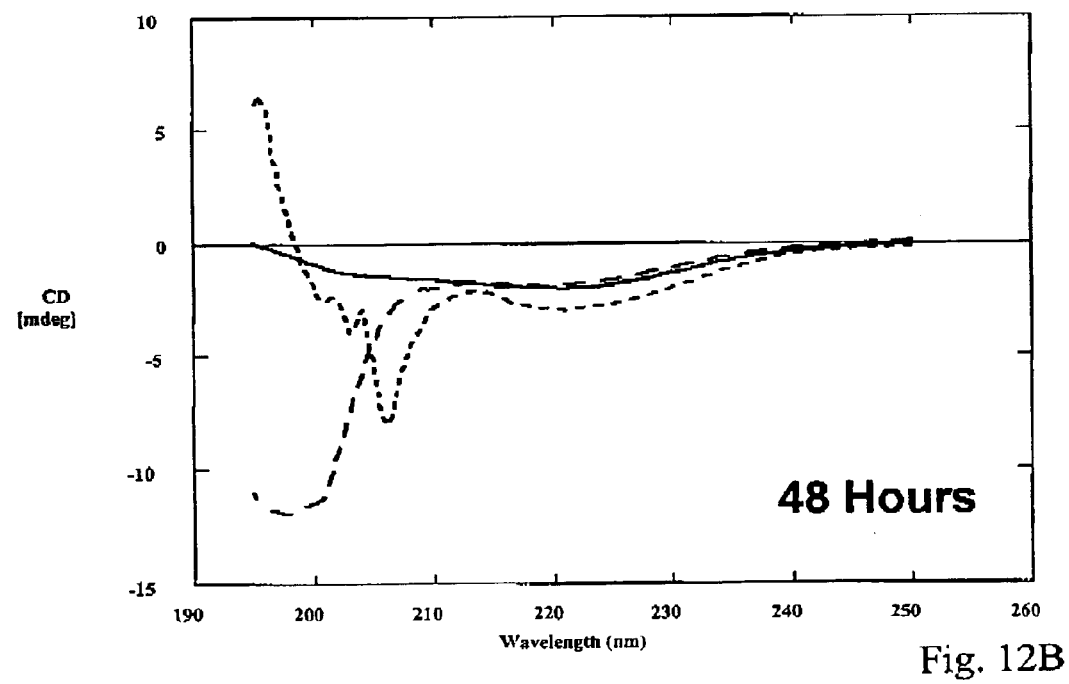
Figure 13A:
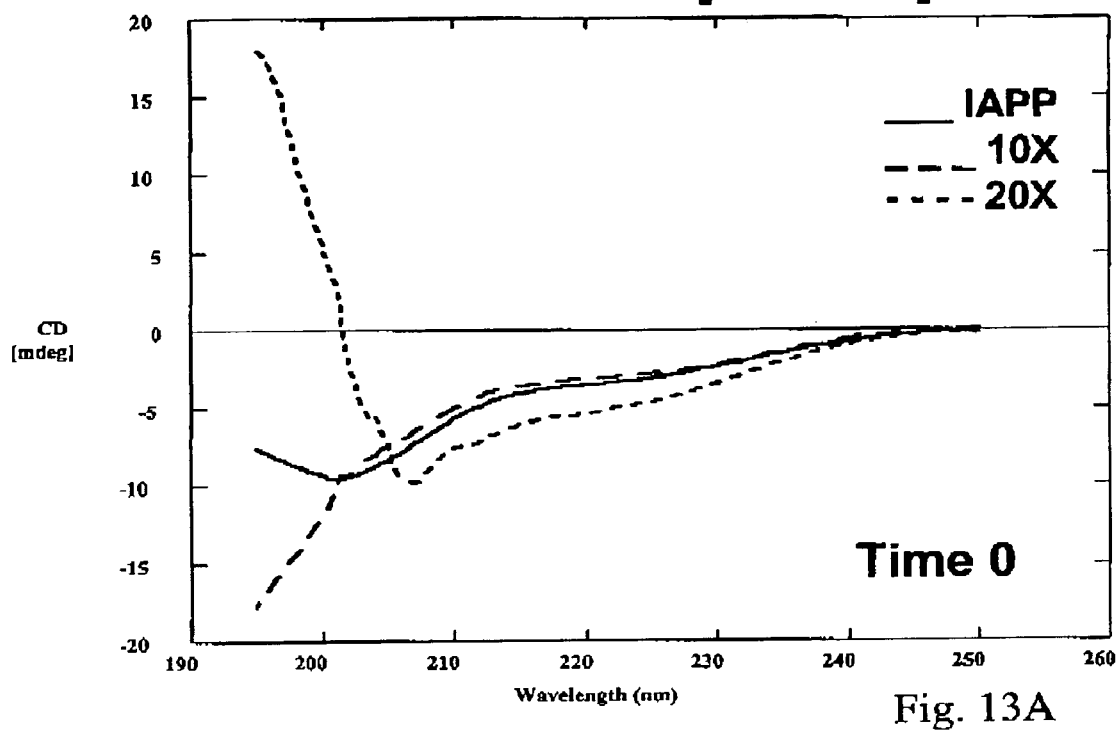
FIGS. 13A and 13B illustrate changes in the conformation of IAPP following incubation with FRA-016 peptide.
Figure 13B:
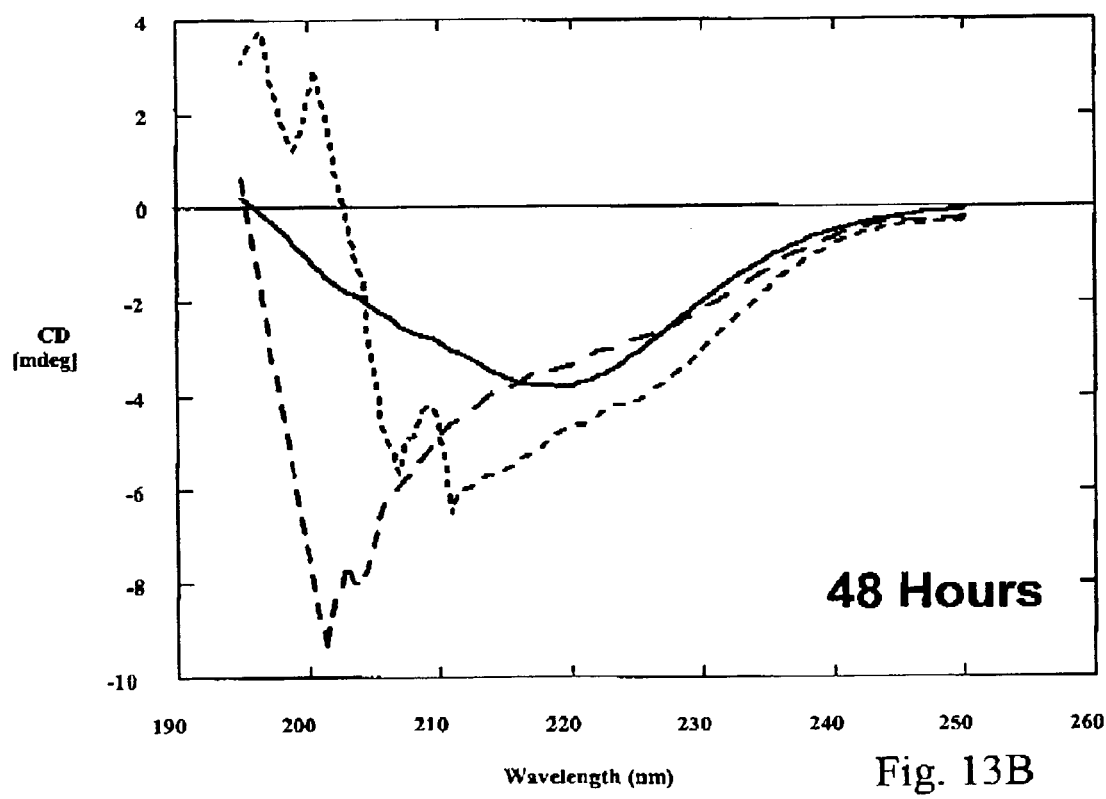
Figure 14A:
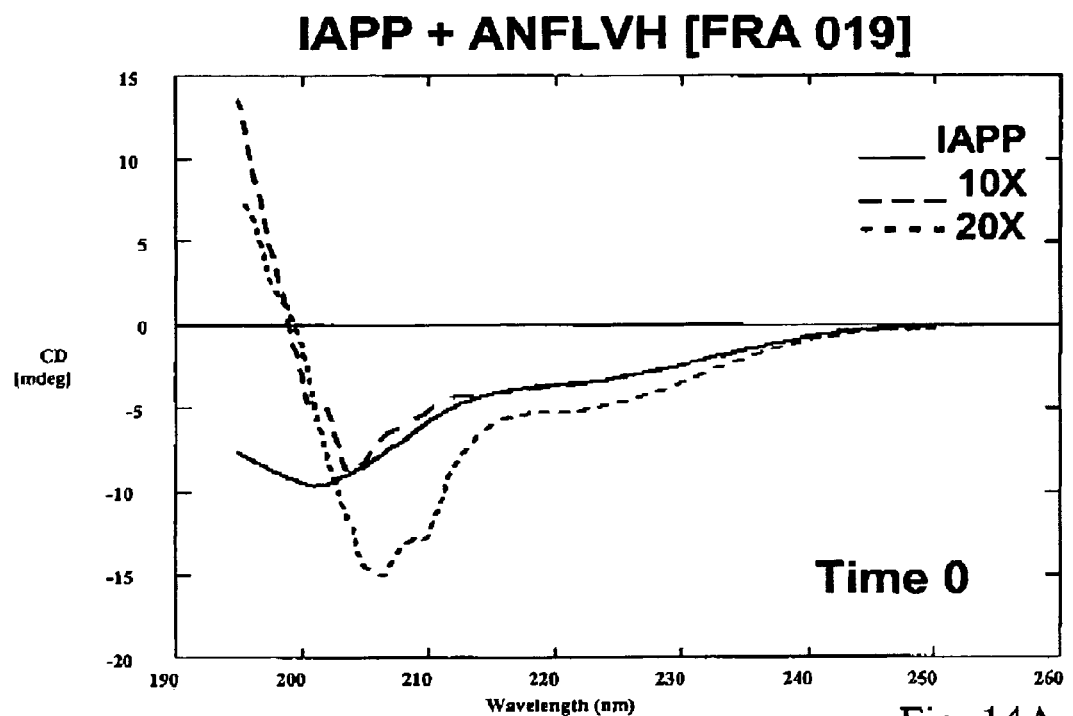
FIGS. 14A and 14B illustrate changes in the conformation of IAPP following incubation with FRA-019 peptide.
Figure 14B:
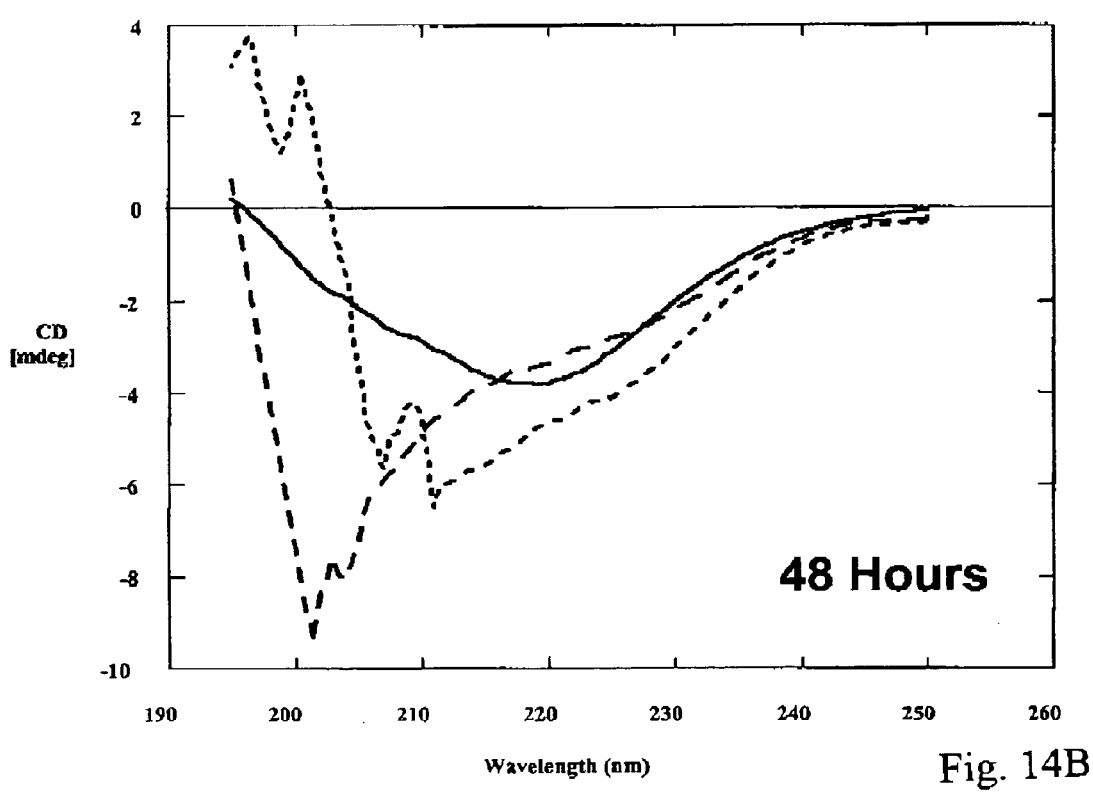
Figure 15A:
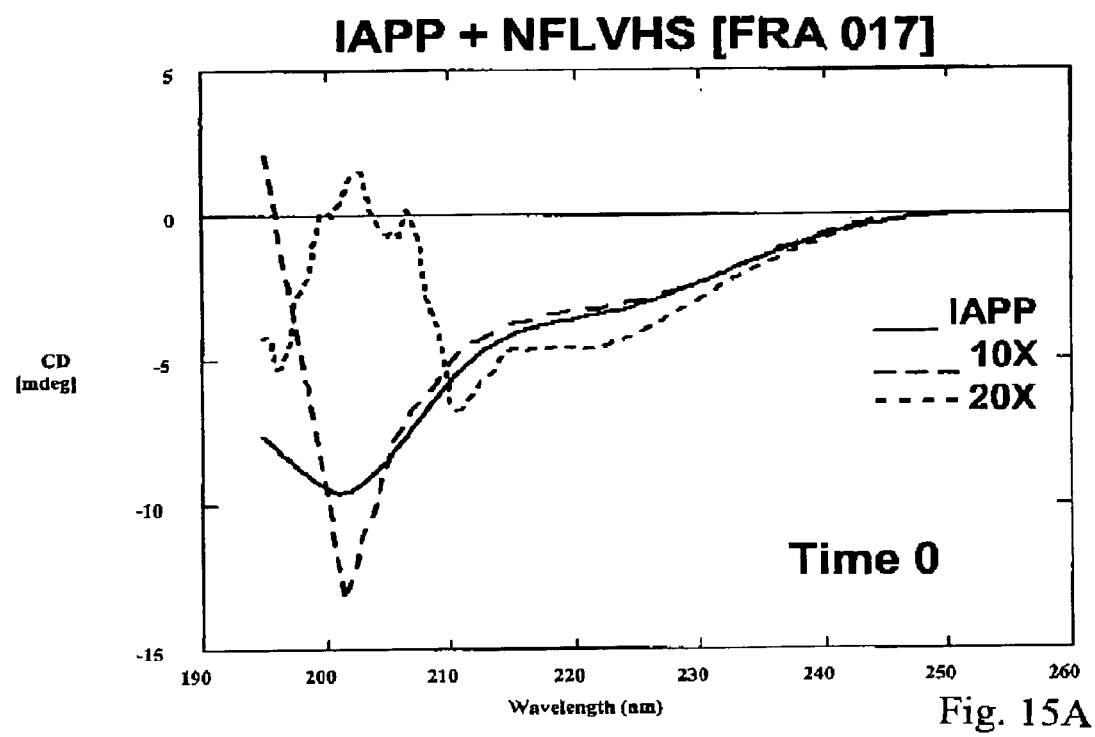
FIGS. 15A and 15B illustrate changes in the conformation of IAPP following incubation with FRA-017 peptide.
Figure 15B:
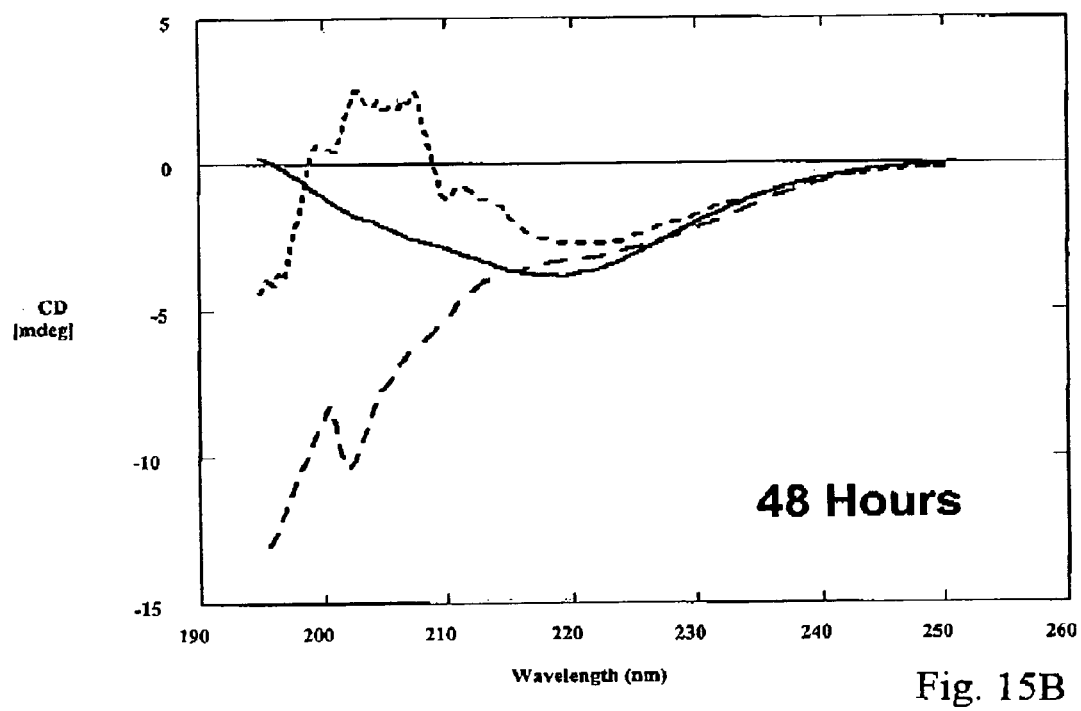
Figure 16A:
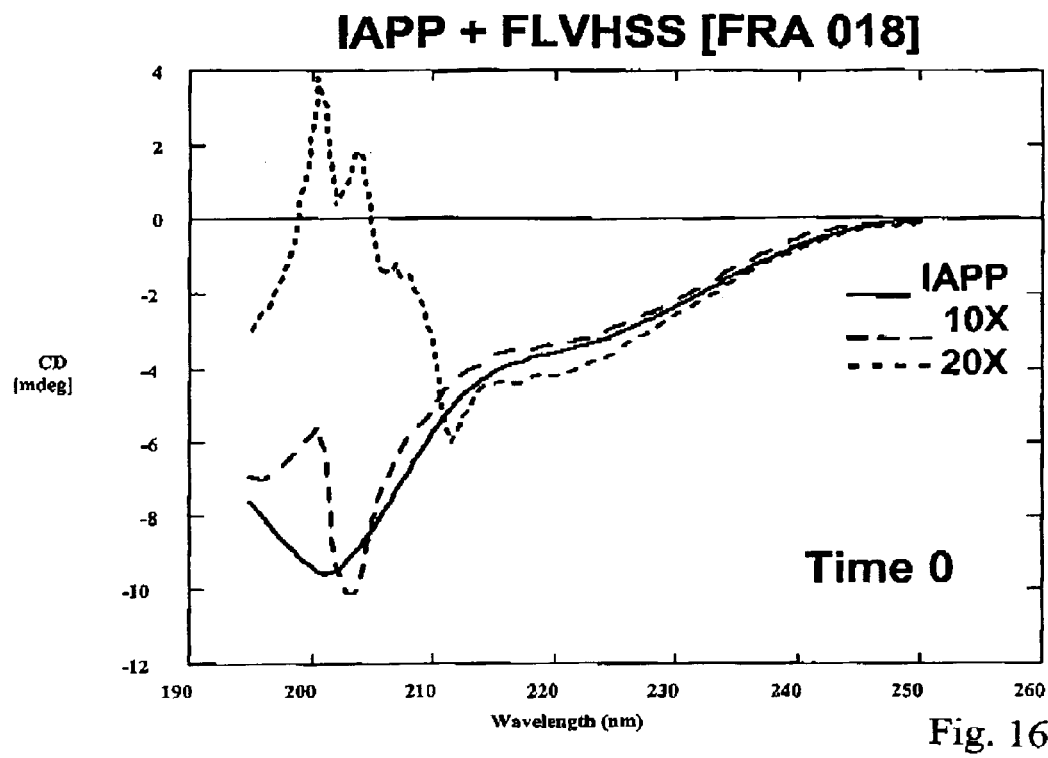
FIGS. 16A and 16B illustrate changes in the conformation of IAPP following incubation with FRA-018 peptide.
Figure 16B:
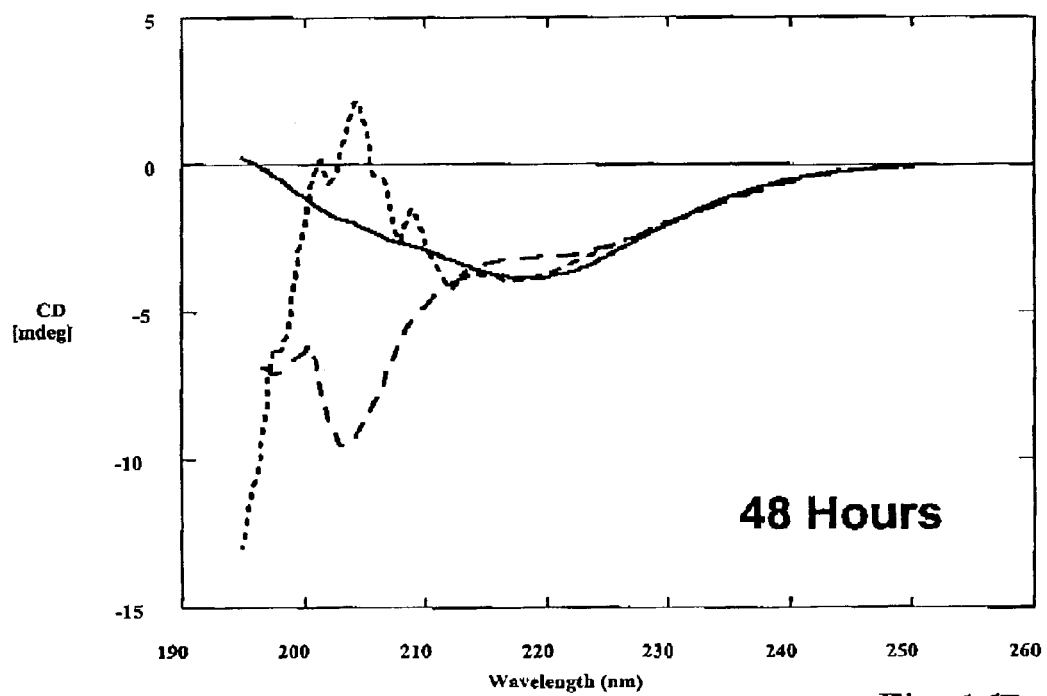
Figure 17B:
FIGS. 17A and 17B illustrate electron micrographs of IAPP fibrils after incubation with FRA-012 peptide at 1:10 (FIG. 17A) or 1:20 (FIG. 17B) dilution.
Figure 17A:
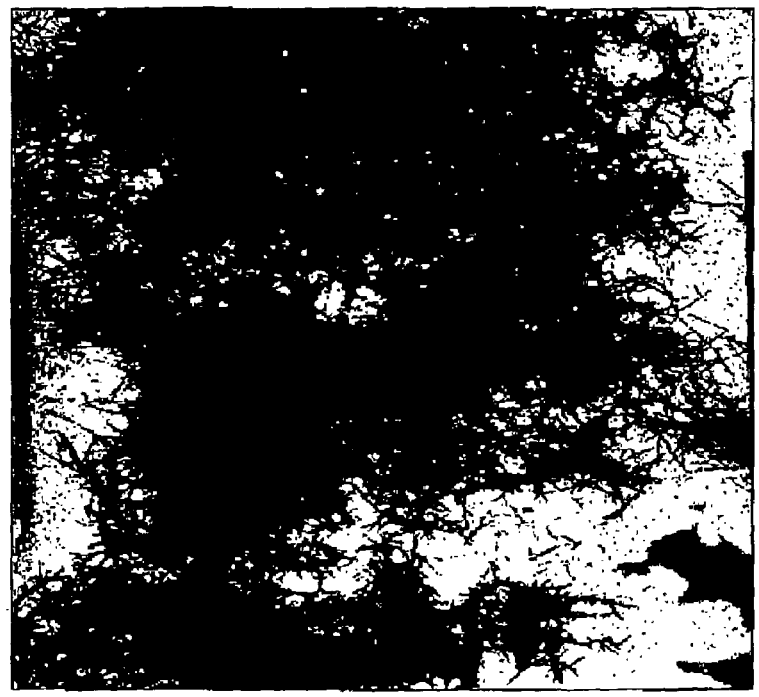

A tyrosine scan was used to determine the amount of soluble hIAPP remaining in solution after a 72-hour incubation. As shown in FIG. 8, the amount of hIAPP alone in solution at time 0 was set at 110%, and all other conditions were normalized to this value. Following a 24-hour incubation, the amount of soluble hIAPP had reduced to 8%. However, when hIAPP was incubated in the presence of peptide SNNFGA (SEQ ID NO. 11), the amount of IAPP remaining in solution was approximately 15%, and in the presence of peptide GAILSS (SEQ ID NO. 14), more than 80% of the hIAPP remained in solution. By 48 hours, the hIAPP incubated alone was no longer soluble and was not detectable using a tyrosine scan. However, approximately 25% of the hIAPP was still measured when co-incubated with either peptide. Similarly, after 72 hours approximately 20% of the hIAPP was still soluble in the sample co-incubated with peptide SNNFGA (SEQ ID NO. 11) or GAILSS (SEQ ID NO. 14).

As detailed previously, hexapeptides derived from the proximal end of hIAPP 20–29 (SSNNFG (SEQ ID NO. 10) and SNNFGA (SEQ ID NO. 11)) were strong inhibitors of β-sheet formation. Incubation of hIAPP (1–37) with either a 1:5 or 1:1 concentration of SNNFGA (SEQ ID NO. 11) was sufficient to prevent β-sheet formation. In addition, while this fragment could not completely inhibit fibril formation, aggregates that were formed displayed an altered morphology and appeared as loosely associated ribbon-like structures. This suggests that the interaction of hIAPP with the Serine and Asparagine residues at the end of these peptides altered normal fibril assembly. When compared to the other peptides (see FIG. 2) the majority of the inhibition appears to be lost once these residues are removed. Therefore, it is likely that these residues have an effect on IAPP fibrillogenesis.

When hIAPP was incubated with peptides targeting the more distal portion of the sequence (20–29), it was found that these fragments were potent inhibitors of β-sheet formation. Peptides GAILSS (SEQ ID NO. 14) and AILSST (SEQ ID NO. 15) were both capable of maintaining the majority of hIAPP in a random coil conformation even at molar ratios as low as 1:5 or 1:1. The morphology of the fibrils that did form in the presence of these peptides was altered; the fibrils formed were less numerous as well as appearing to be elongated thin threads as opposed to the densely packed groups of fibrils observed when hIAPP is incubated alone.

It has been suggested that a lack of clearance of IAPP following secretion (Clodi, M., et al., *Am. J. Physiol.* 274: E903–E908, 1998) and/or an incomplete processing of pro-IAPP in patients with Type-II diabetes may provide an environment that enhances fibrillogenesis (Higham, C E., et al., *Eur. J. Biochem.* 267: 4998–5004, 2000). One possibility is that the overabundance of IAPP could act as "seeds" for fibrillar assembly and aggregation (Higham, C E., et al., *Eur. J. Biochem.* 267: 4998–5004, 2000; Kahn, S E., et al., *Diabetes* 46: 1725–1727, 1997; and Clark, A., et al., *Diabetologia* 36: A136, 1993). It was observed that when hIAPP was incubated in the presence of inhibitory peptides SSNNFG (SEQ ID NO. 10), SNNFGA (SEQ ID NO. 11), GAILSS (SEQ ID NO. 14),and AILSST (SEQ ID NO. 15), that along with other changes to morphology, there was an absence of fibrillar aggregates which could act as seeds for extra fibrillar assembly. These data were also supported by sedimentation experiments that demonstrated that the inhibitory peptides SNNFGA (SEQ ID NO. 11) and GAILSS (SEQ ID NO. 14) were able to maintain IAPP in a soluble form for a longer period of time, and thereby attenuated the formation of fibrillar aggregates. This could be thought of as an additional inhibitory effect of the hexapeptides since not only are the fibrils less likely to form the typical dense meshes of insoluble hIAPP, it may be more difficult for hIAPP aggregates to form at all in the absence of these nucleating seeds. Further support of this seeding hypothesis was observed when IAPP was incubated with the short peptide NFGAIL (SEQ ID NO. 19). The immediate increase in the development of fibrils in the presence of this short peptide demonstrates the capacity of certain peptides to enhance fibrillogenesis.

IAPP Toxicity Assay

RIN-1056A cells were plated into 96 well plates at a density of $2 \times 10^4$ cells/well in Dulbecco's Modified Eagle Medium (DMEM) (Gibco-BRL) supplemented with 5% Fetal calf serum (Gibco-BRL), 100 U/ml penicillin (Gibco-BRL), and 100 U/ml streptomycin (Gibco-BRL). After an initial 24 h of culture, cells received fresh medium containing 10 μM hIAPP or rat IAPP alone, or in combination with 200 μM SNNFGA (SEQ ID NO. 11). Cells in control wells received fresh medium only. Cells were incubated with peptide at 37° C., 5% $CO_2$, for 24 hours, after which alamar Blue (1/10th volume) was added to each well. Cells were incubated in the presence of alamar Blue (MEDICORP, Montreal) for a period of 8 hours, and data was collected at 2 hour intervals. The fluorescence of the samples was measured using a SpectraMAX Gemini XS Microplate Spectrofluorometer (Molecular Devices) with an excitation wavelength of 544 um and an emission wavelength of 590 nm. Data were collected using the SoftMax Pro 3.1 software for MacIntosh.

Results

Figure 25A:
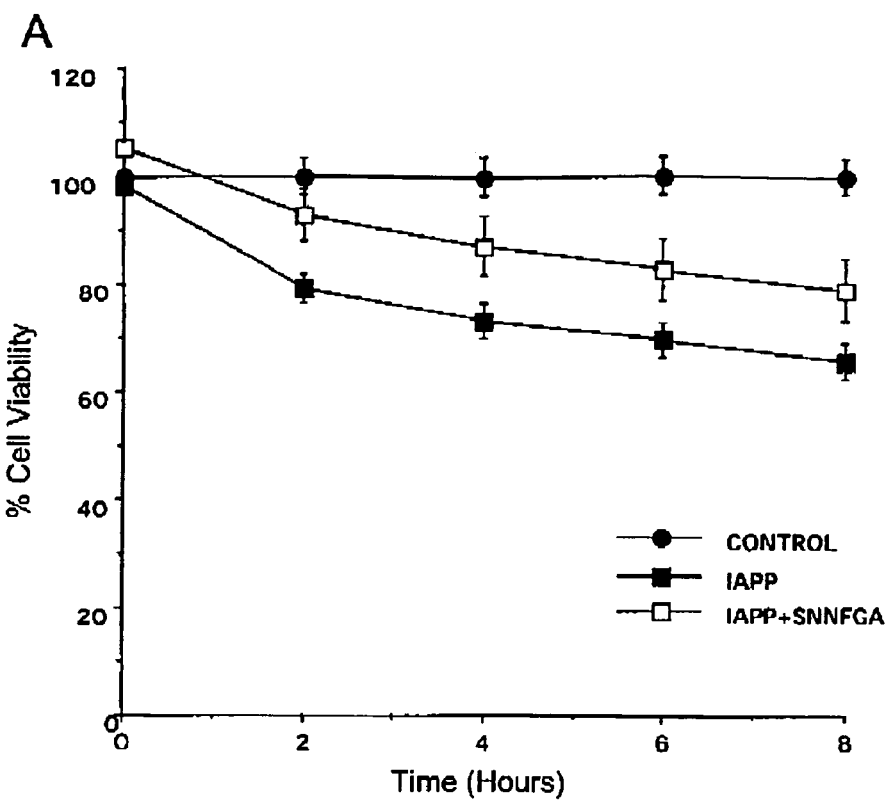
FIGS. 25A and 25B illustrate toxicity of a peptide of the present invention.
Figure 25B:
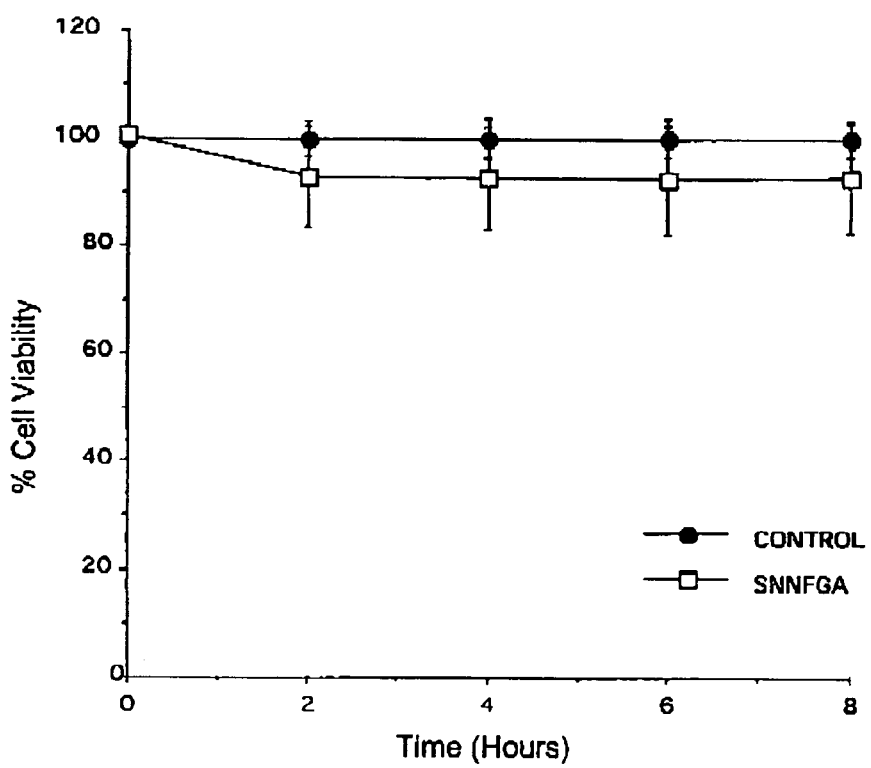

The toxicity of hIAPP fibrils on pancreatic β cell lines has been well documented. Experiments were carried out to determine whether the inhibitory peptide SNNFGA (SEQ ID NO. 11) could not only inhibit fibril formation but also decrease the cytotoxic effects of hIAPP fibrils on pancreatic β cells. RIN2056 cells were incubated for 24 hours in the presence of 10 μM hIAPP alone or in the presence of the peptide SNNFGA (SEQ ID NO. 11). An alamar Blue assay was used to quantitatively measure the proliferation of the cells, and compare the cytotoxic effects of various additives to the cultures. As shown in FIG. 25A, the addition of hIAPP to RIN1056 cells produced a 35–40% decrease in cell viability compared to cells in culture medium alone (controls). Co-incubation of peptide SNNFGA (SEQ ID NO. 11) with hIAPP resulted in a significant improvement in cell viability compared to hIAPP alone. In addition, it was also observed that this peptide is not directly toxic to pancreatic p cells in culture (FIG. 25B).

Peptides derived from the 8–20 region of IAPP

Similar experiments as detailed previously have been conducted with the following peptides derived from the 8 to 20 region of IAPP (see FIG. 2):

| | | |
|---|---|---|
| ATQRLA | (SEQ ID NO.5) | [FRA-012] |
| TQRLAN | (SEQ ID NO.22) | [FRA-013] |
| QRLANF | (SEQ ID NO.23) | [FRA-014] |
| RLANFL | (SEQ ID NO.24) | [FRA-015] |
| LANFLV | (SEQ ID NO.6) | [FRA-016] |
| ANFLVH | (SEQ ID NO.7) | [FRA-019] |
| NFLVHS | (SEQ ID NO.8) | [FRA-017] |
| FLVHSS | (SEQ ID NO.9) | [FRA-018] |

These peptides were tested for their effects on conformation. From the circular dichroism results, and as can be seen on FIGS. 9A to 16B, only the peptides FRA-012, FRA-016, FRA-019, FRA-017, and FRA-018 have inhibitory activity. In fact, Fra-012 displayed limited inhibition at higher concentration. Fra-013 displayed enhanced formation of the beta-sheet conformation at a 10-fold molar excess but possibility of a random coil at higher concentrations; however the signal is highly attenuated so this might be the result of extensive precipitation at the higher concentrations. Fra-014 displayed similar behavior to that seen for FRA-013. FRA-015 displayed enhanced lateral aggregation (ribbon structures) similar to FRA-013 and FRA-014. Fra-016 displayed relatively good inhibition as shown by retention of the majority of the IAPP peptide as a random coil at a 10-fold molar excess. However, FRA-016 displayed a better activity at higher concentrations. FRA-019 maintained a random coil inhibition and appears to be similar to the LANFLV (SEQ ID NO. 6) (FRA-016) in terms of activity. FRA-017 displayed limited inhibitory activity. FRA-018 displayed some modest inhibition (comparable to FRA-019 and FRA-017).

CD findings were confirmed by negative stain electron microscopy, which demonstrated that the peptides fell into defined groups (see FIGS. 17A to 24B).

When tested for their ability to increase or decrease aggregation, FRA-013, FRA-014, and FRA-015 significantly accelerated aggregation and produced fibrils that were large, twisted structures. These were not observed in the control IAPP and were similar to those typically seen upon the addition of a glycosaminoglycan in the case of Aβ. FRA-012 and FRA-017 had only limited effects on the density and morphology of the fibrils that were formed.

Figures 21A, 21B:
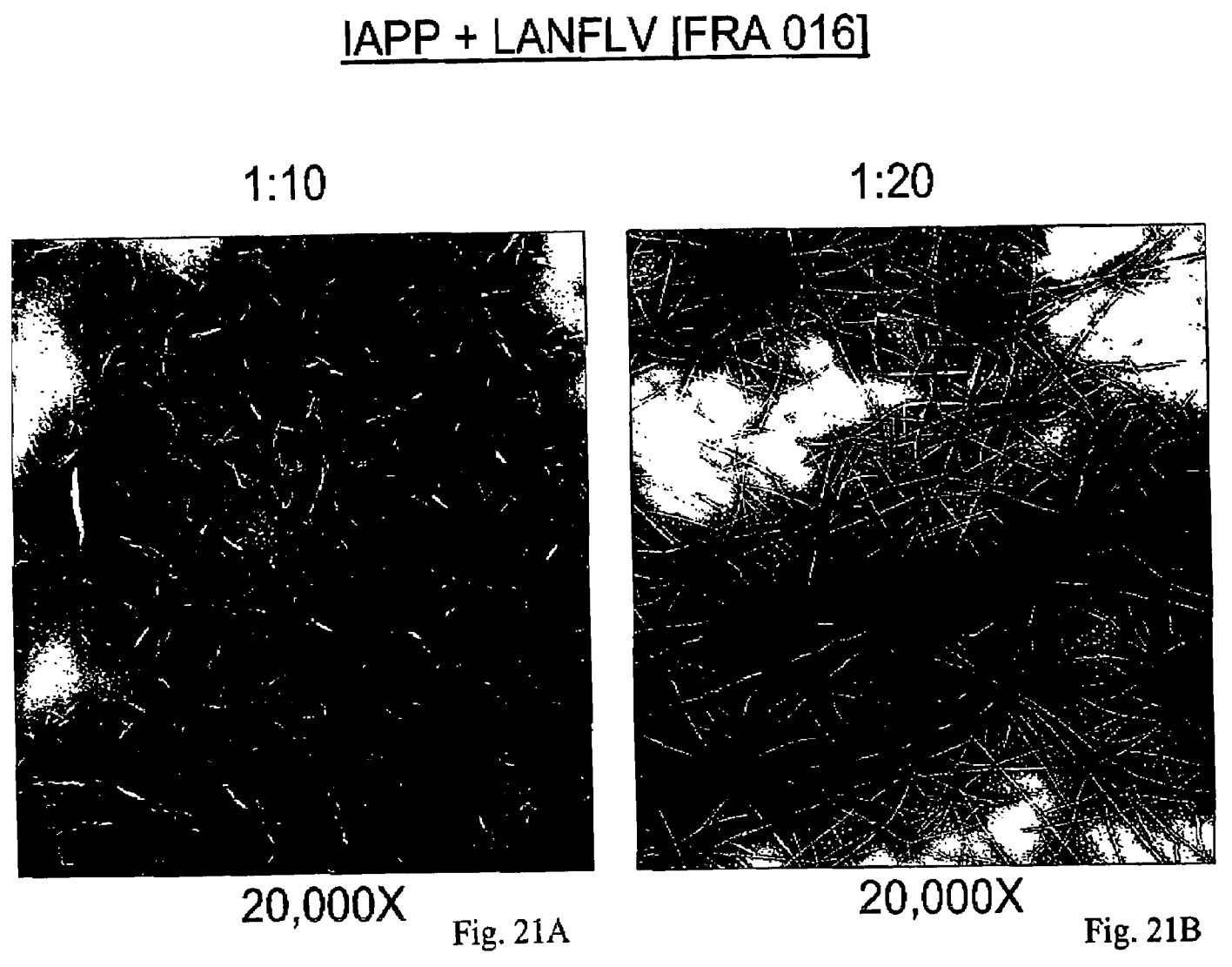

EM of FRA-016 demonstrated the disruption of normal fibrils at 10-fold excess to produce only truncated, semi-fibrillar aggregates (see FIGS. 21A and 21B. Some fibrils were also seen at the 20-fold molar ratio.

For FRA-019, the inhibition (see FIGS. 22A and 22B) was confirmed with lower density of IAPP fibrils and morphology was of much thinner protofibrils, which is consistent with the CD results.

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method for the treatment of islet amyloid polypeptide (IAPP)-related amyloidosis disorders in a patient, comprising administering to said patient a therapeutically effective amount of an antifibrillogenic agent that consists of a hexapeptide of the sequence of SEQ ID NO:7 or SEQ ID NO:8.

2. The method of claim 1, wherein said islet amyloid polypeptide (IAPP)-related amyloidosis disorder is Type II diabetes.

3. A method for the treatment of islet amyloid polypeptide (IAPP)-related amyloidosis disorders in a patient, comprising administering to said patient a therapeutically effective amount of a composition comprising (i) an antifibrillogenic agent that consists of a hexapeptide of the sequence of SEQ ID NO:7 or SEQ ID NO:8, and (ii) a pharmaceutically acceptable carrier.

4. The method of claim 3, wherein said islet amyloid polypeptide (IAPP)-related amyloidosis disorder is Type II diabetes.

5. The method of claim 3, wherein said composition is administered in conjunction with another agent selected from the group consisting of insulin, sulfonylurea and glucose sensitizers.

6. A method for inhibiting islet amyloid polypeptide (IAPP)-related amyloidosis or for cytoprotection, comprising administering to a subject a therapeutically effective amount of an antifibrillogenic agent that consists of a hexapeptide of the sequence of SEQ ID NO:7 or SEQ ID NO:8, wherein said antifibrillogenic agent prevents or reduces islet amyloid polypeptide (IAPP) deposition.

7. The method of claim 6, wherein said islet amyloid polypeptide (IAPP)-related amyloidosis or islet amyloid polypeptide (IAPP) deposition is Type II diabetes.

8. The method of claim 6, wherein said antifibrillogenic agent is administered in conjunction with another agent selected from the group consisting of insulin, sulfonylurea and glucose sensitizers.

9. The method of claim 1, wherein the sequence of said hexapeptide is SEQ ID NO:7.

10. The method of claim 1, wherein the sequence of said hexapeptide is SEQ ID NO:8.

11. The method of claim 1, wherein said islet amyloid polypeptide (IAPP)-related amyloidosis disorder is Type I diabetes.

12. The method of claim 3, wherein said islet amyloid polypeptide (IAPP)-related amyloidosis disorder is Type I diabetes.

13. The method of claim 6, wherein said islet amyloid polypeptide (IAPP)-related amyloidosis or islet amyloid polypeptide (IAPP) deposition is Type I diabetes.

14. A method for the treatment of Type II diabetes in a patient, comprising administering to the patient a therapeutically effective amount of an antifibrillogenic agent that consists of a hexapeptide of the sequence of SEQ ID NO:7 or SEQ ID NO:8.

15. A method for the treatment of Type II diabetes in a patient, comprising administering to the patient a therapeutically effective amount of a composition comprising (i) an antifibrillogenic agent that consists of a hexapeptide of the sequence of SEQ ID NO:7 or SEQ ID NO:8, and (ii) a pharmaceutically acceptable carrier.

16. A method for inhibiting islet amyloid polypeptide (IAPP)-related amyloidosis in Type II diabetes or for cytoprotection, comprising administering to a subject a therapeutically effective amount of an antifibrillogenic agent that consists of a hexapeptide of the sequence of SEQ ID NO:7 or SEQ ID NO:8, wherein said antifibrillogenic agent prevents or reduces islet amyloid polypeptide (IAPP) deposition.

* * * * *

SEQUENCE LISTING

```
<160> NUMBER OF SEQ ID NOS: 27

<210> SEQ ID NO 1
<211> LENGTH: 26
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 1

Ala Thr Gln Arg Leu Ala Asn Phe Leu Val His Ser Ser Ser Ser Asn
 1               5                  10                  15

Asn Phe Gly Ala Ile Leu Ser Ser Thr Asn
            20                  25

<210> SEQ ID NO 2
<211> LENGTH: 13
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 2

Ala Thr Gln Arg Leu Ala Asn Phe Leu Val His Ser Ser
 1               5                  10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 3

Asn Val Gly Ser Asn Thr Tyr
 1               5
```

<210> SEQ ID NO 4
<211> LENGTH: 13
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 4

Ser Ser Asn Asn Phe Gly Ala Ile Leu Ser Ser Thr Asn
 1               5                  10

<210> SEQ ID NO 5
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 5

Ala Thr Gln Arg Leu Ala
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 6

Leu Ala Asn Phe Leu Val
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 7

Ala Asn Phe Leu Val His
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 8

Asn Phe Leu Val His Ser
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

```
<400> SEQUENCE: 9

Phe Leu Val His Ser Ser
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 10

Ser Ser Asn Asn Phe Gly
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 11

Ser Asn Asn Phe Gly Ala
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 12

Asn Asn Phe Gly Ala Ile
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 13

Phe Gly Ala Ile Leu Ser
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 14

Gly Ala Ile Leu Ser Ser
 1               5

<210> SEQ ID NO 15
<211> LENGTH: 6
<212> TYPE: PRT
```

```
<213> ORGANISM: Artificial Sequence
<220> FEATURE:
<223> OTHER INFORMATION: Description of Artificial
      Sequence:Antifibrillogenic agents

<400> SEQUENCE: 15

Ala Ile Leu Ser Ser Thr
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 16

Ile Leu Ser Ser Thr Asn
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 17

Asn Val Gly Ser Asn Thr
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 18

Val Gly Ser Asn Thr Tyr
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 19

Asn Phe Gly Ala Ile Leu
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 20

Gly Ala Ile Leu Ser Ser Thr
 1               5
```

<210> SEQ ID NO 21
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 21

Ser Ser Asn Phe Gly Ala
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 22

Thr Gln Arg Leu Ala Asn
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 23

Gln Arg Leu Ala Asn Phe
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 24

Arg Leu Ala Asn Phe Leu
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial
      Sequence:Antifibrillogenic agents

<400> SEQUENCE: 25

Lys Leu Val Phe Phe Ala
 1               5

<210> SEQ ID NO 26
<211> LENGTH: 42
<212> TYPE: PRT
<213> ORGANISM: Homo sapiens

<400> SEQUENCE: 26

-continued

```
Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Primary
      sequence of IAPP

<400> SEQUENCE: 27

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
            20                  25                  30

Gly Ser Asn Thr Tyr
        35
```